United States Patent
Iguchi

(10) Patent No.: US 10,149,606 B2
(45) Date of Patent: Dec. 11, 2018

(54) OPTICAL UNIT AND ENDOSCOPE

(71) Applicant: OLYMPUS CORPORATION, Tokyo (JP)

(72) Inventor: Takehiko Iguchi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 64 days.

(21) Appl. No.: 15/606,444

(22) Filed: May 26, 2017

(65) Prior Publication Data

US 2017/0258303 A1 Sep. 14, 2017

Related U.S. Application Data

(63) Continuation of application No. PCT/JP2014/083559, filed on Dec. 18, 2014.

(51) Int. Cl.
*G02B 7/02* (2006.01)
*A61B 1/00* (2006.01)
(Continued)

(52) U.S. Cl.
CPC ........ *A61B 1/00188* (2013.01); *A61B 1/0057* (2013.01); *A61B 1/00114* (2013.01);
(Continued)

(58) Field of Classification Search
CPC ..... A61B 1/00188; A61B 1/04; A61B 1/0057; A61B 1/00117; A61B 1/00114;
(Continued)

(56) References Cited

U.S. PATENT DOCUMENTS

| 7,940,482 B2 | 5/2011 | Sato | |
|---|---|---|---|
| 2007/0149855 A1* | 6/2007 | Noguchi | A61B 1/00096 600/168 |
| 2009/0296241 A1 | 12/2009 | Sato | |
| 2013/0027534 A1 | 1/2013 | Kibayashi | |

FOREIGN PATENT DOCUMENTS

| JP | H02-301023 A | 12/1990 |
|---|---|---|
| JP | H05-196850 A | 8/1993 |

(Continued)

OTHER PUBLICATIONS

International Search Report dated Mar. 31, 2015 issued in PCT/JP2014/083559.

*Primary Examiner* — Alicia M Harrington
(74) *Attorney, Agent, or Firm* — Scully, Scott, Murphy & Presser, P.C.

(57) ABSTRACT

An optical unit 1 includes a voice coil motor 10 which can relatively move a movable part 3 with respect to a fixed part 2 in the axis C direction by using a coil 11 arranged on the fixed part 2 and a magnet 12 arranged on the movable part 3, wherein the movable part 3 includes a movable-side sliding surface which can slide over an inner periphery of the fixed part 2, and a distance L1 from a position closest to an object side to a position closest to an image side of the movable-side sliding surface in the axis C direction of the movable part 3 is greater than a distance from an emission surface of the object-side fixed lens group Gf held by the fixed part 2 to an incident surface of the image-side fixed lens group Gb held by the fixed part 2.

18 Claims, 23 Drawing Sheets

(51) Int. Cl.
     *G02B 23/26*   (2006.01)
     *A61B 1/005*   (2006.01)
     *A61B 1/04*    (2006.01)
     *G02B 7/09*    (2006.01)
     *H02K 41/035*  (2006.01)
     *G02B 7/08*    (2006.01)
     *G02B 23/24*   (2006.01)
     *H04N 5/225*   (2006.01)

(52) U.S. Cl.
     CPC .......... *A61B 1/00117* (2013.01); *A61B 1/04* (2013.01); *G02B 7/08* (2013.01); *G02B 7/09* (2013.01); *G02B 23/243* (2013.01); *G02B 23/26* (2013.01); *H02K 41/0356* (2013.01); *H04N 5/2254* (2013.01); *H04N 2005/2255* (2013.01)

(58) Field of Classification Search
     CPC ......... H04N 5/2254; H04N 2005/2255; G02B 7/09; G02B 23/243; G02B 7/08; G02B 23/26; H02K 41/0356
     See application file for complete search history.

(56) References Cited

FOREIGN PATENT DOCUMENTS

| | | |
|---|---|---|
| JP | 5031666 B | 9/2012 |
| JP | 2014-002349 A | 1/2014 |
| WO | WO 2012/137739 A1 | 10/2012 |

\* cited by examiner (b)

(a)

OPTICAL UNIT AND ENDOSCOPE

CROSS-REFERENCE TO RELATED APPLICATIONS

This application is based on PCT/JP2014/083559 filed on Dec. 18, 2014. The contents of the PCT application is incorporated herein by reference.

BACKGROUND OF THE INVENTION AND RELATED ART STATEMENT

The present invention relates to an optical unit and an endoscope in which a movable part is driven to move back and forth by using a voice coil motor.

In general, an optical unit having an autofocus function or motor-driven zoom function uses a driving device for driving a movable part holding a focusing or zooming moving lens to move back and forth in an optical axis direction. For example, a technique for using an electromagnetic actuator using a coil and magnets, i.e., a voice coil motor as the driving device has conventionally been disclosed (see Japanese Patent No. 5,031,666).

SUMMARY OF INVENTION

An optical unit according to an aspect of the present invention includes:

a fixed part that holds at least either an object-side fixed lens group or an image-side fixed lens group and has a cylindrical shape about a predetermined axis at least in part;

a movable part that holds a moving lens group between the object-side fixed lens group and the image-side fixed lens group, is arranged radially inside the fixed part, and has a cylindrical shape about the axis; and a voice coil motor that is capable of relatively moving the movable part with respect to the fixed part in the axial direction by using a coil arranged on the fixed part and a magnet arranged on the movable part, the magnet being magnetically polarized in a direction orthogonal to the axis, wherein the movable part includes a movable-side sliding surface that is capable of sliding over an inner periphery of the fixed part, and a distance from a position closest to an object side to a position closest to an image side of the movable-side sliding surface in the axial direction of the movable part is greater than a distance from an emission surface of the object-side fixed lens group held by the fixed part to an incident surface of the image-side fixed lens group held by the fixed part.

DESCRIPTION OF EMBODIMENTS

Hereinafter, an optical unit according to the present embodiment will be described.

Figure 1:
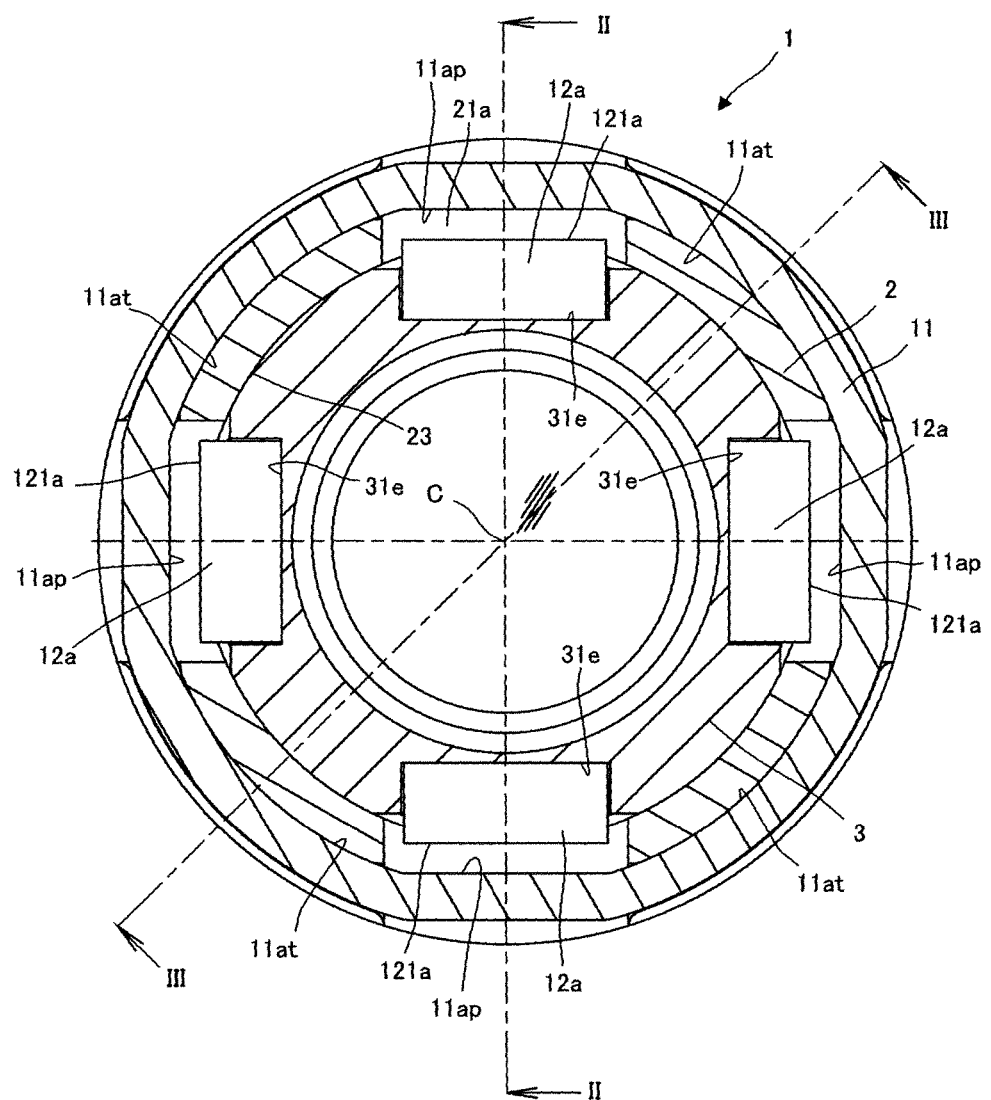
FIG. 1 is a cross-sectional view illustrating an optical unit according to a first embodiment.
Figure 2:
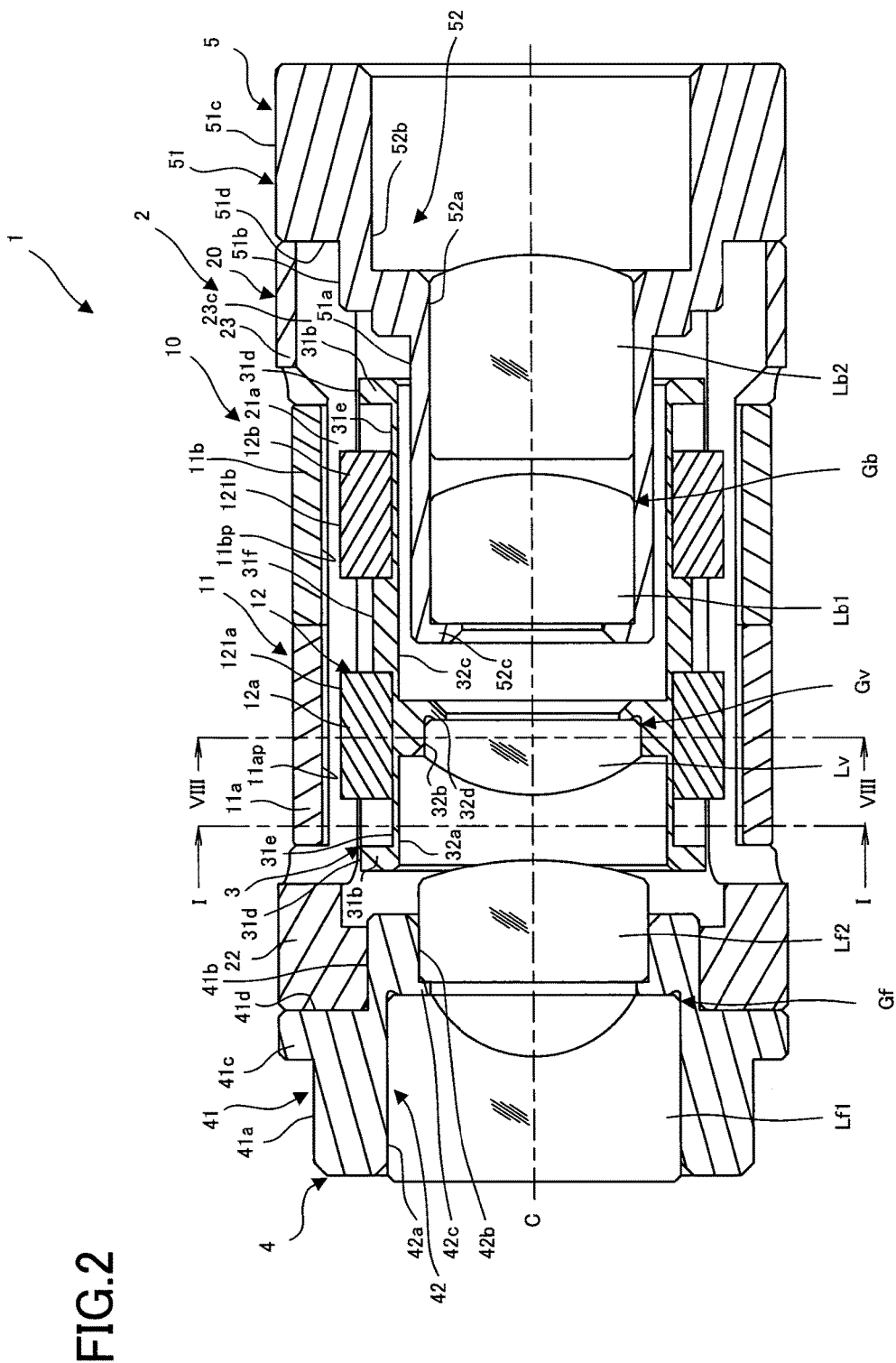
FIG. 2 is a cross-sectional view taken along the line II-II of FIG. 1.
Figure 3:
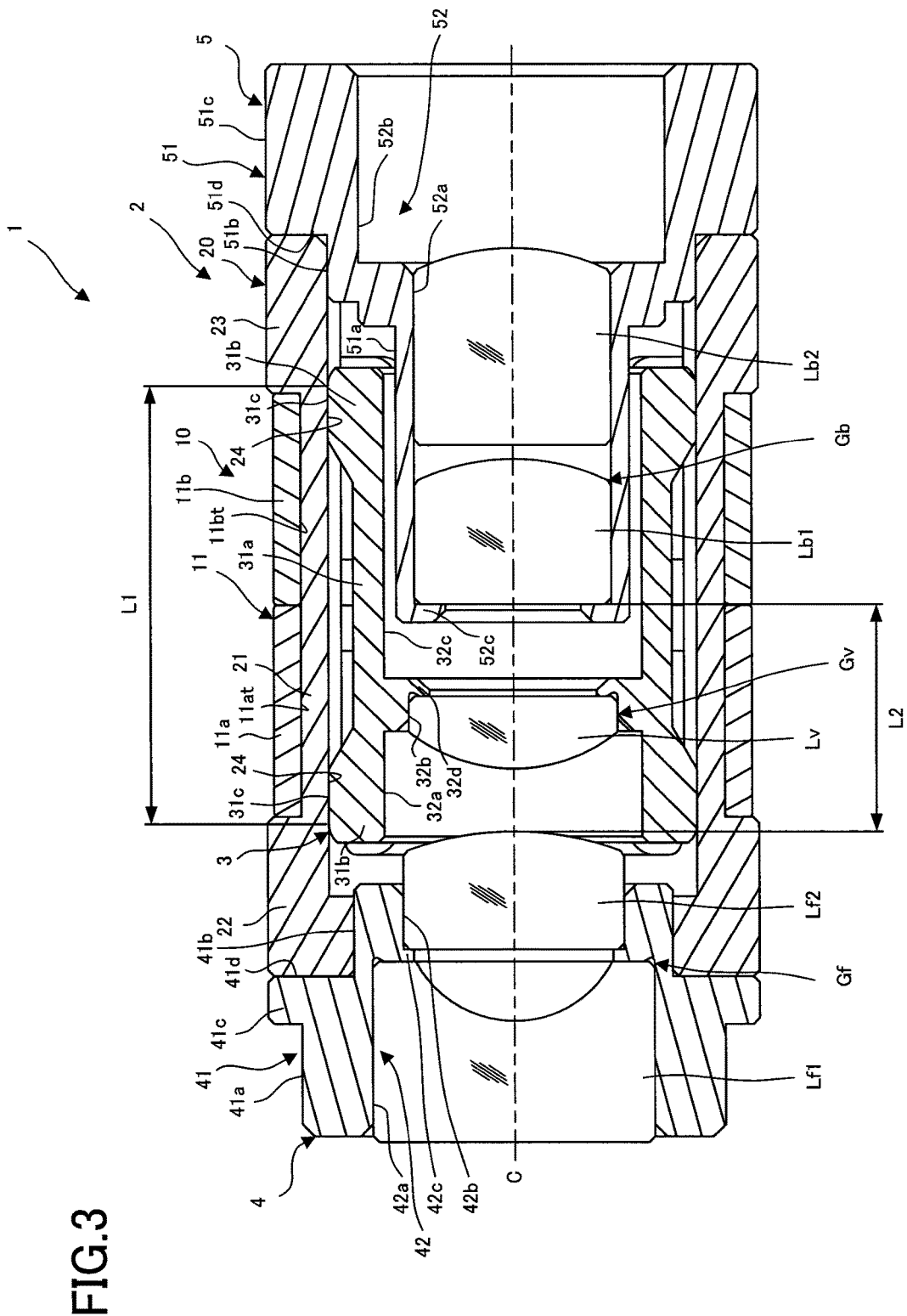
FIG. 3 is a cross-sectional view taken along the line of FIG. 1.

FIG. 1 is a cross-sectional view illustrating an optical unit according to a first embodiment. FIG. 2 is a cross-sectional view taken along the line II-II of FIG. 1. FIG. 3 is a cross-sectional view taken along the line of FIG. 1. FIG. 1 is also a cross-sectional view taken along the line I-I of FIG. 2.

As illustrated in FIGS. 2 and 3, an optical unit 1 according to the present embodiment includes a fixed part 2, a movable part 3 which is movable with respect to the fixed part 2 and holds a moving lens group Gv, and a voice coil motor 10 which generates driving force for moving the movable part 3 with respect to the fixed part 2.

In the optical unit 1 according to the first embodiment, the fixed part 2 includes a fixed part main body 20, a front frame portion 4 which holds an object-side fixed lens group Gf lying on an object side of the moving lens group Gv and is attached to an object side of the fixed part main body 20, and a rear frame portion 5 which holds an image-side fixed lens group Gb lying on an image side of the moving lens group Gv and is attached to an image side of the fixed part main body 20.

Figure 4:
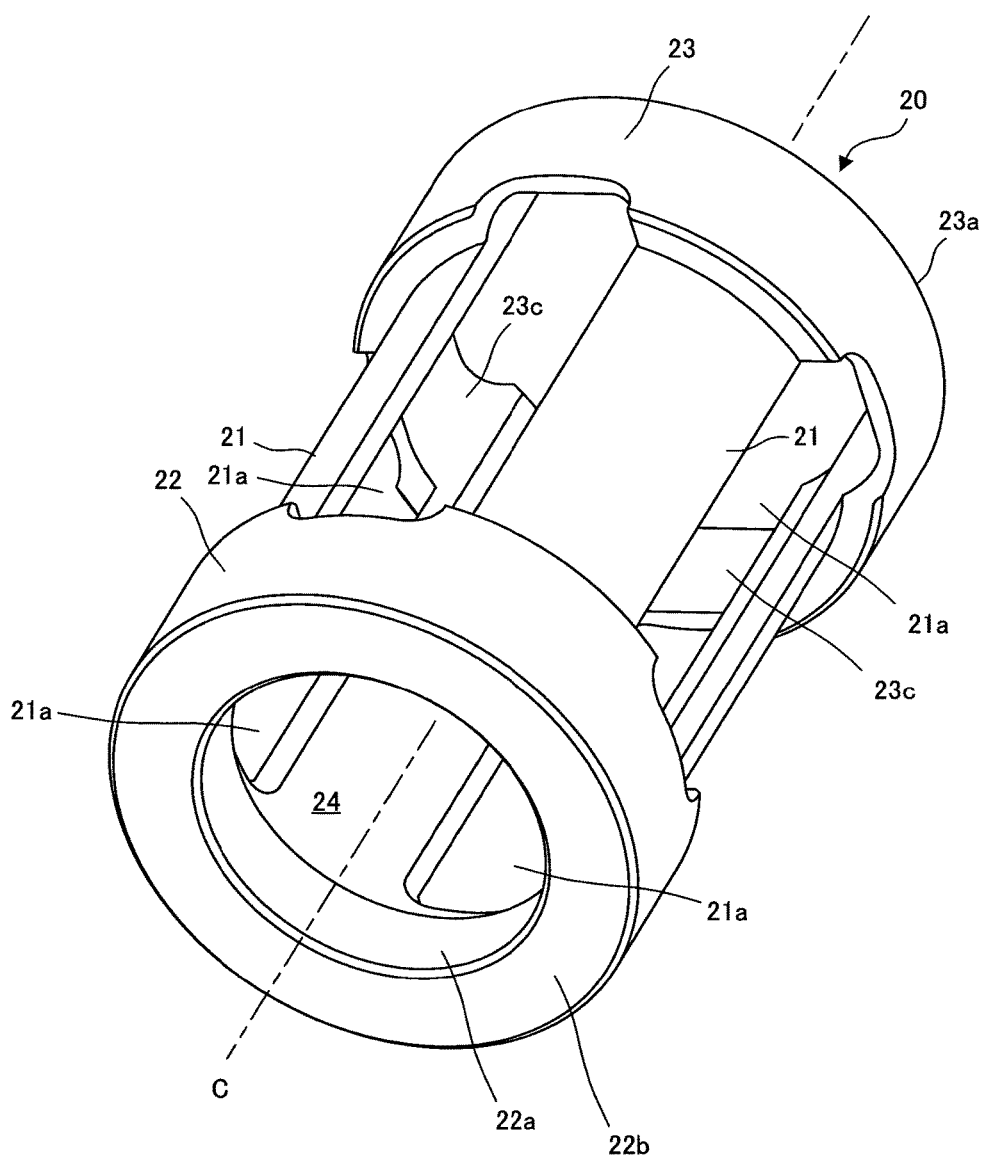
FIG. 4 is a diagram illustrating a fixed part main body of the optical unit according to the first embodiment.

FIG. 4 is a diagram illustrating the fixed part main body of the optical unit according to the first embodiment.

As illustrated in FIG. 3, the fixed part main body 20 includes a member having a cylindrical shape about a predetermined axis C at least in part. The fixed part main body 20 according to the first embodiment includes a cylindrical portion 21 about the axis C, and an object-side thick portion 22 which are formed on an object side of the cylindrical portion 21 in the axial direction and an image-side thick portion 23.

The cylindrical portion 21 includes hollowed portions 21a in part. In the first embodiment, four hollowed portions 21a are formed at intervals of 90° about the axis C of the cylindrical portion 21. The radial inner surface of the cylindrical portion 21 except the hollowed portions 21a is a cylindrical surface of cylindrical shape and serves as a fixed-side sliding surface 24 for guiding and supporting the movable part 3. The fixed-side sliding surface 24 is thus shaped to be circumferentially divided by the hollowed portions 21a.

The object-side thick portion 22 is formed to protrude radially outward and radially inward from the cylindrical portion 21. The image-side thick portion 23 is formed to protrude radially outward from the cylindrical portion 21. Grooves 23c are formed in the fixed-side sliding surface 24 on the radially inner side of the image-side thick portion 23. When the movable part 3 is assembled, magnets 12 to be described later pass through the grooves 23c. This enables smooth assembly of the movable part 3 to the fixed part main body 20. The thick portions 22 and 23 may be formed as members separate from the cylindrical portion 21 and attached during assembly.

Figure 5B:
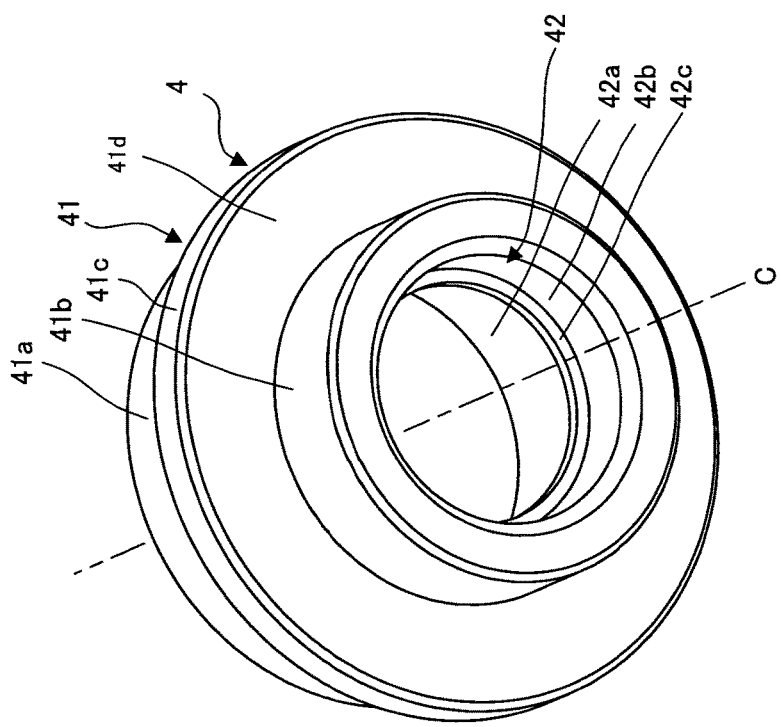
FIGS. 5A and 5B are a diagram illustrating a front frame portion of the optical unit according to the first embodiment.
Figure 5A:
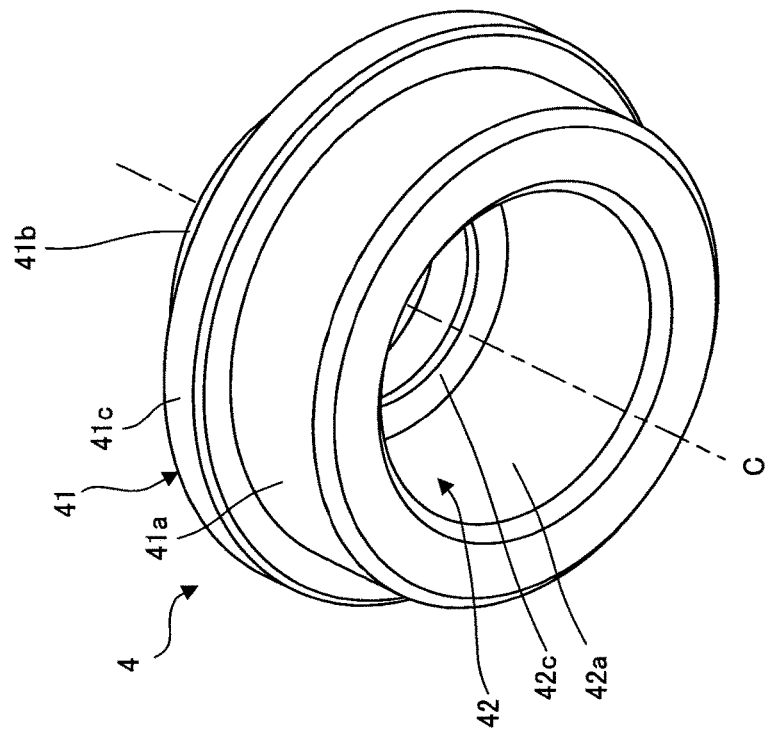

FIGS. 5A and 5B are diagrams illustrating the front frame portion of the optical unit according to the first embodiment.

The front frame portion 4 is a cylindrical member including an outer peripheral portion 41 and an inner peripheral portion 42. The outer peripheral portion 41 includes a first outer peripheral portion 41a, a second outer peripheral portion 41b, and an outer periphery-side protrusion 41c. The inner peripheral portion 42 includes a first inner peripheral portion 42a, a second inner peripheral portion 42b, and an inner periphery-side protrusion 42c.

The first outer peripheral portion 41a has a diameter larger than that of the second outer peripheral portion 41b. The outer periphery-side protrusion 41c having the largest diameter, protruding radially outward, lies between the first outer peripheral portion 41a and the second outer peripheral portion 41b. The first inner peripheral portion 42a has a diameter larger than that of the second inner peripheral portion 42b. The inner periphery-side protrusion 42c having the smallest diameter, protruding radially inward, lies between the first inner peripheral portion 42a and the second inner peripheral portion 42b.

The front frame portion 4 holds the object-side fixed lens group Gf. For example, in the first embodiment, the front frame portion 4 holds a front first lens Lf1 in the first inner peripheral portion 42a and a front second lens Lf2 in the second inner peripheral portion 42b. The image side of the front first lens Lf1 and the object side of the front second lens Lf2 are preferably held in contact with the protrusion 42c.

The front frame portion 4 is inserted with the second outer peripheral portion 41b in contact with an inner periphery 22a of the object-side thick portion 22 of the fixed part main body 20 until an object-side end surface 22b of the fixed part main body 20 comes into contact with a step portion 41d between the second outer peripheral portion 41b and the outer periphery-side protrusion 41c.

Figure 6B:
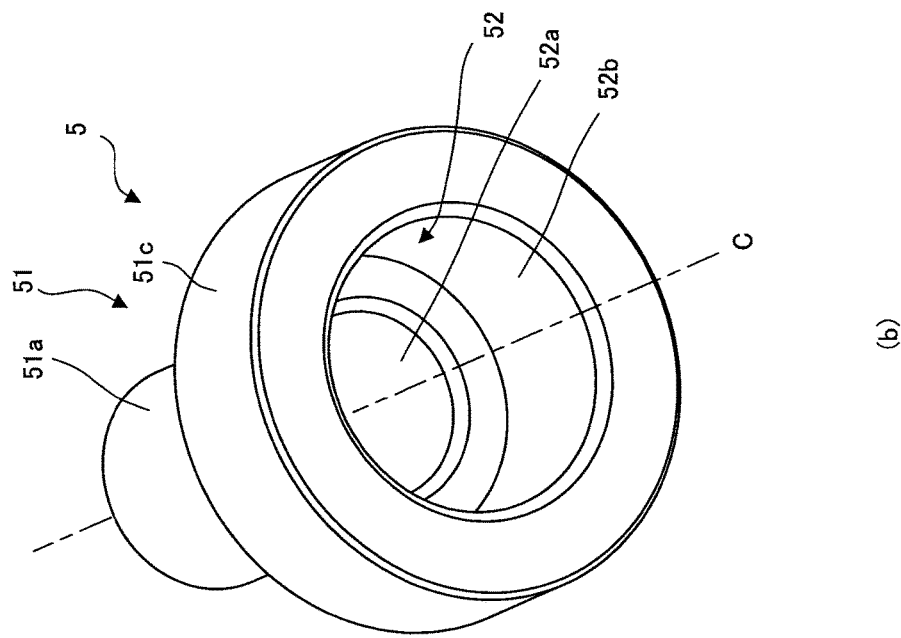
FIGS. 6A and 6B are a diagram illustrating a rear frame portion of the optical unit according to the first embodiment.
Figure 6A:
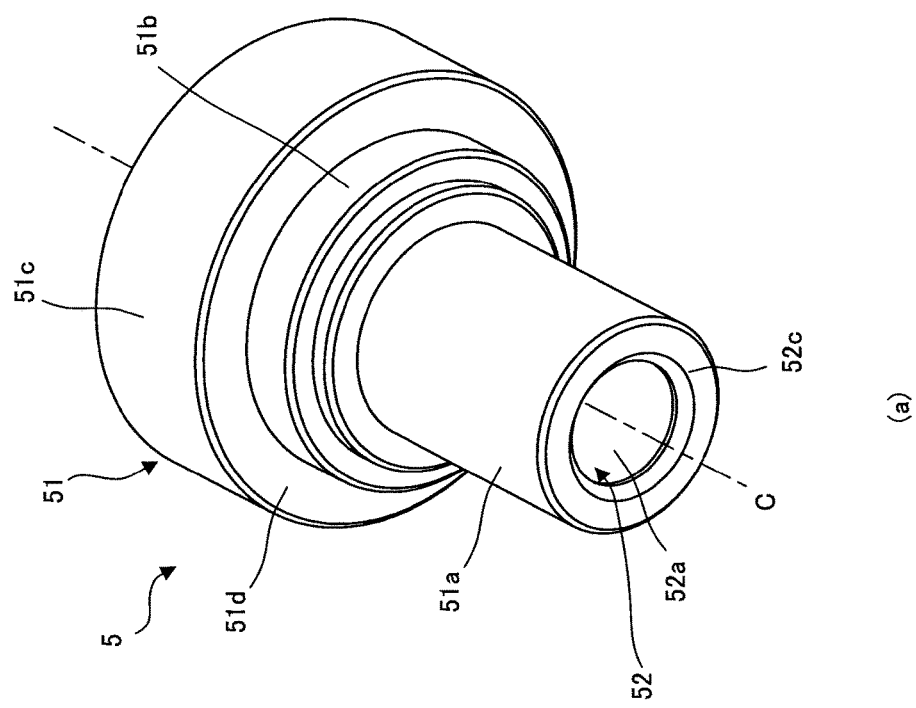

FIGS. 6A and 5B are diagrams illustrating the rear frame portion of the optical unit according to the first embodiment.

The rear friend unit 5 is a cylindrical member including an outer peripheral portion 51 and an inner peripheral portion 52. The outer peripheral portion 51 includes a first outer peripheral portion 51a, a second outer peripheral portion 51b, and a third outer peripheral portion 51c. The inner peripheral portion 52 includes a first inner peripheral portion 52a, a second inner peripheral portion 52b, and an inner periphery-side protrusion 52c.

The first outer peripheral portion 51a has a diameter smaller than that of the second outer peripheral portion 51b, and the second outer peripheral portion 51b has a diameter smaller than that of the third outer peripheral portion 51c. The first inner peripheral portion 52a has a diameter smaller than that of the second inner peripheral portion 52b. The inner periphery-side protrusion 52c having the smallest diameter, protruding radially inward, lies at an end closest to the object side of the first inner peripheral portion 52a.

The rear frame portion 5 holds the image-side fixed lens group Gb. For example, in the first embodiment, the rear frame portion 5 holds a rear first lens Lb1 and a rear second lens Lb2 in the first inner peripheral portion 52a. The object side of the rear first lens Lb1 is preferably held in contact with the inner periphery-side protrusion 52c.

The rear frame portion 5 is inserted with the second outer peripheral portion 51b in contact with the fixed-side sliding surface 24 of the image-side thick portion 23 of the fixed part main body 20 until an image-side end surface 23a of the fixed part main body 20 comes into contact with a step portion 51d between the second outer peripheral portion 51b and the third outer peripheral portion 51c.

Figure 7:
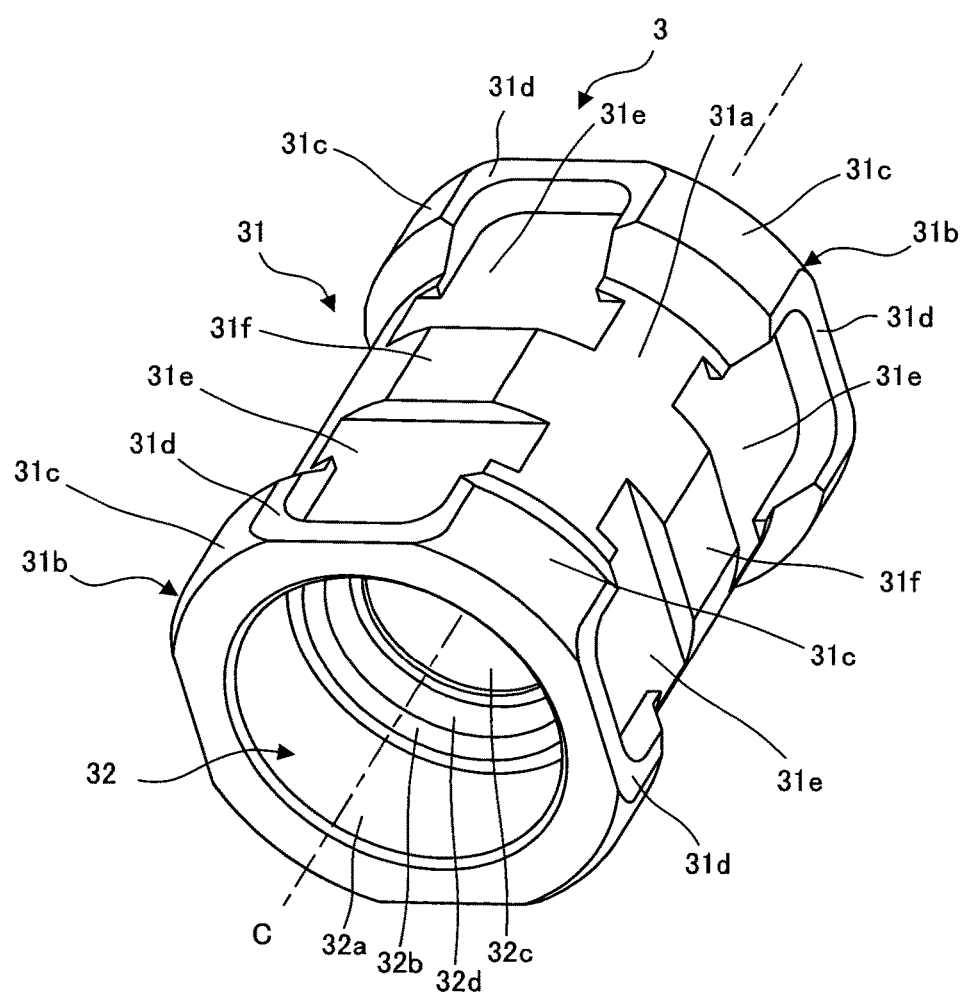
FIG. 7 is a diagram illustrating a movable part of the optical unit according to the first embodiment.

FIG. 7 is a diagram illustrating the movable part of the optical unit according to the first embodiment.

As illustrated in FIG. 7, the movable part 3 according to the first embodiment includes a cylindrical member including an outer peripheral portion 31 and an inner peripheral portion 32 with the predetermined axis C at the center.

The outer peripheral portion 31 of the movable part 3 includes a cylindrical portion 31a, flange portions 31b which are formed on both ends of the cylindrical portion 31a in the axis C direction and have an outer peripheral diameter larger than that of the cylindrical portion 31a, a movable-side sliding surface 31c which includes outer peripheries of the flange portions 31b, flat surface portions 31d which are formed on part of radially outer sides of the flange portions 31b, step portions 31e which are formed between the flat surface portions 31d at both ends in the axis C direction and on a radially inner side of the cylindrical portion 31a, and cut portions 31f which are formed between the step portions 31e in the axial direction by cutting away the surface of the cylindrical portion 31a. The cylindrical portion 31a and the flange portions 31b of the movable part 3 may be configured as separate members to be assembled.

The inner peripheral portion 32 of the movable part 3 includes a first inner peripheral portion 32a, a second inner peripheral portion 32b, a third inner peripheral portion 32c, and a protrusion 32d. The second inner peripheral portion 32b has a diameter smaller than those of the first inner peripheral portion 32a and the third inner peripheral portion 32c. The inner periphery-side protrusion 32d having the smallest diameter, protruding radially inward, lies between the second inner peripheral portion 32b and the third inner peripheral portion 32c.

The movable part 3 holds the moving lens group Gv. For example, in the first embodiment, the movable part 3 holds a moving lens Lv in the second inner peripheral portion 32b. The image side of the moving lens Lv is preferably held in contact with the inner periphery-side protrusion 32d.

The outer peripheries of the flange portions 31b of the movable part 3 constitute the movable-side sliding surface 31c which slides over the fixed-side sliding surface 24 of the fixed part main body 20. The movable part 3 is inserted into the fixed part main body 20 with the movable-side sliding surface 31c in contact with the fixed-side sliding surface 24. In the first embodiment, as illustrated in FIGS. 2 and 3, the movable part 3 is inserted so that the first outer peripheral portion 51a of the rear frame portion 5 is opposed to the radially inner side of the third inner peripheral portion 32c of the movable part 3. In other words, at least part of the image-side fixed lens group Gb lies radially inside the third inner peripheral portion 32c of the movable part 3. If the movable part 3 moves closest to the object side, at least part of the object-side fixed lens group Gf lies radially inside the first inner peripheral portion 32a of the movable part 3.

In the optical unit 1 according to the first embodiment, as illustrated in FIG. 3, the distance L1 from the position closest to the object side to the position closest to the image side of the movable-side sliding surface 31c of the movable part 3 in the axis C direction is greater than the distance L2 from the emission surface of the object-side fixed lens group Gf held by the front frame portion 4 of the fixed part 2 to the incident surface of the image-side fixed lens group Gb held by the rear frame portion 5 of the fixed part 2. Note that the chamfered portions are not included in the distance from the position closest to the object side to the position closest to the image side of the movable-side sliding surface 31c of the movable part 3.

Such a configuration allows miniaturization in the axis C direction. A tilt of the movable part 3 can be suppressed to allow miniaturization in the radial direction as well.

As illustrated in FIG. 2, the voice coil motor 10 includes a coil 11 which is arranged on the fixed part main body 20 of the fixed part 2, and magnets 12 which are arranged on the movable part 3 so as to be opposed to the coil 11.

As illustrated in FIG. 3, the coil 11 according to the present embodiment includes a first coil 11a which is wound around the outer periphery of the cylindrical portion 21 of the fixed part main body 20, and a second coil 11b which is wound around the outer periphery of the cylindrical portion 21 of the fixed part main body 20 to adjoin the first coil 11a in the axis C direction. The coil 11 may be wound in advance and attached afterward. The first coil 11a and the second coil 11b adjoining in the axis C direction are preferably connected in series, but may be connected in parallel. As illustrated in FIGS. 1 and 2, the first coil 11a and the second coil 11b include flat surfaces 11ap and 11bp corresponding to the hollowed portions 21a of the fixed part main body 20, respectively. More specifically, the first coil 11a and the second coil 11b include the flat surface portions 11ap and 11bp and cylindrical portions 11at and 11bt which are alternately arranged in the circumferential direction, respectively.

As illustrated in FIGS. 1 and 2, the magnets 12 include first magnets 12a and second magnets 12b which are arranged to axially adjoin the step portions 31e of the movable part 3 at every 90° about the axial center so as to be opposed to the inner sides of the flat surface portions 11ap and 11bp of the first coil 11a and the second coil 11b, respectively. The first magnets 12a and the second magnets 12b can thus be stably installed to form a stable magnetic field and suppress deviations of the movable part 3 moving with respect to the fixed part 2.

The sum of the widths of the first coils 11a and the second coils 11b in the axis C direction is preferably set to be greater than the width across the first magnets 12a and the second magnets 12b in the axis C direction, and so that the first magnets 12a and the second magnets 12b always remain within the widths of the first coils 11a and the second coils 11b in the axis C direction, respectively, in the movable range of the movable part 3.

In the present embodiment, the magnets 12 are installed at every 90° about the axis C. However, a plurality of magnets may be installed at different angles, not limited to 90°.

Figure 8:
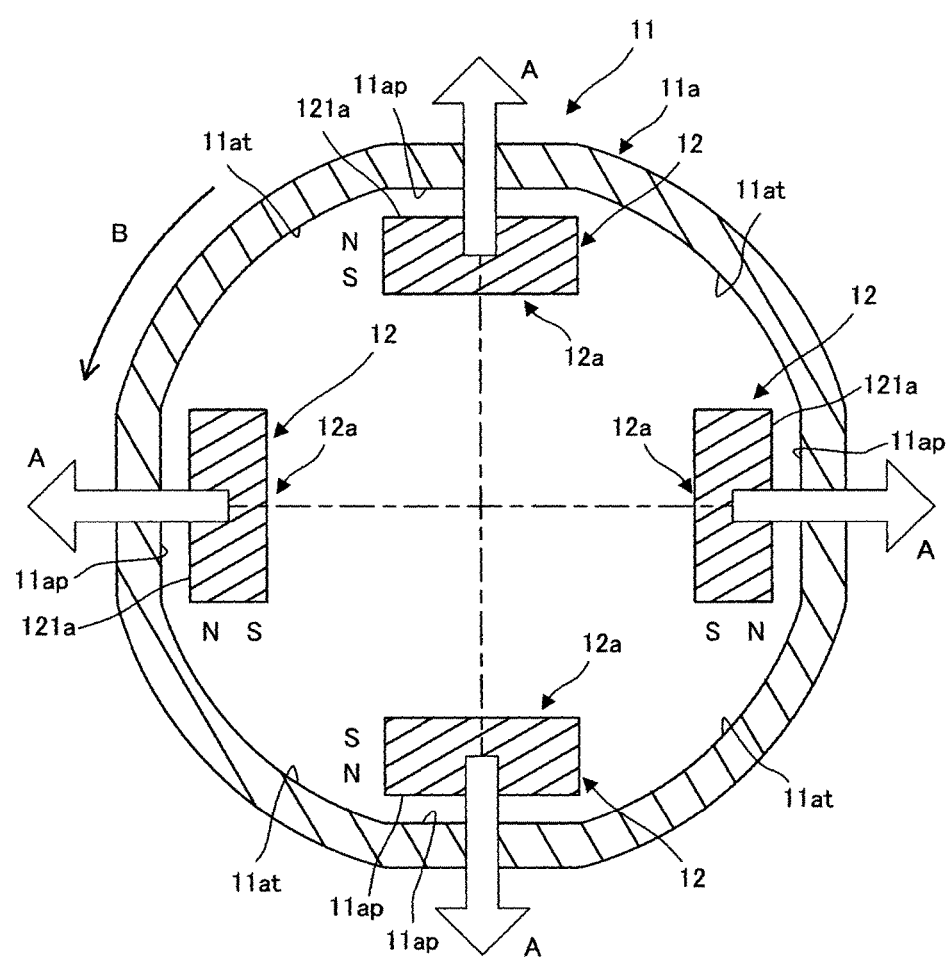
FIG. 8 is a cross-sectional view taken along the line VIII-VIII of FIG. 2, illustrating only a voice coil motor.
Figure 9:
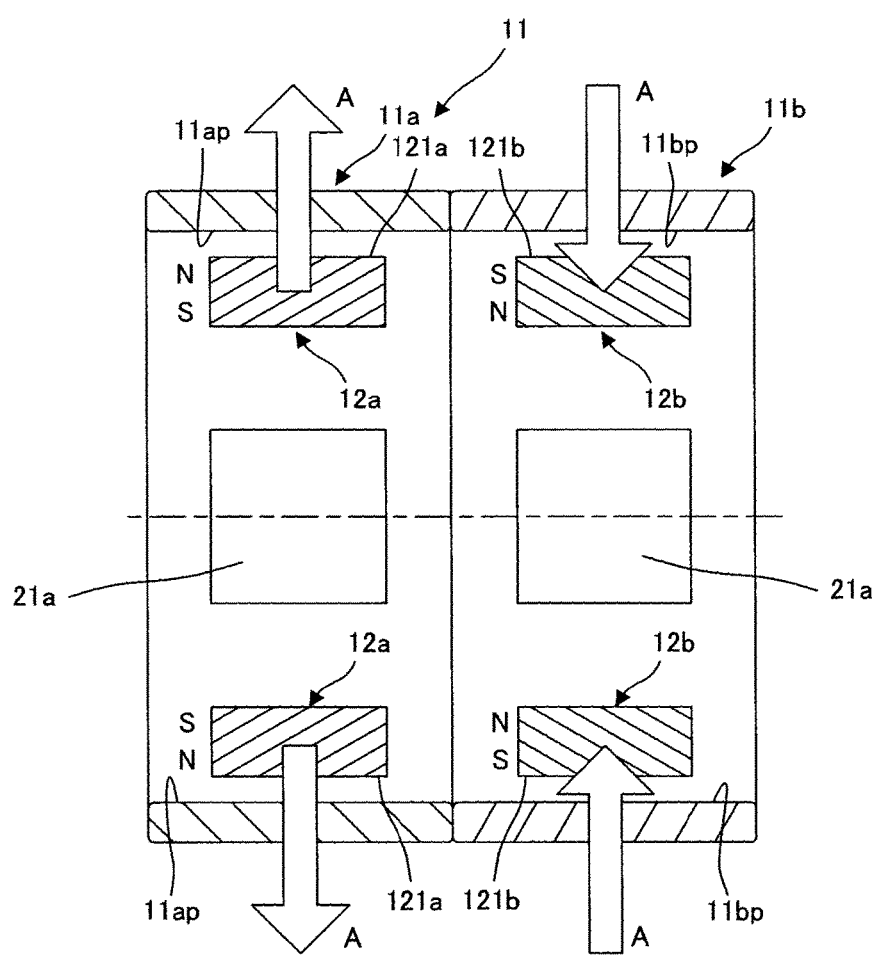
FIG. 9 is a cross-sectional view illustrating only the voice coil motor of FIG. 2.

FIG. 8 is a cross-sectional view taken along the line VIII-VIII of FIG. 1, illustrating only the voice coil motor. FIG. 9 is a cross-sectional view illustrating only the voice coil motor of FIG. 2.

In the present embodiment, the magnets 12 are arranged so that the group of first magnets 12a and the group of second magnets 12b are separated in the axis C direction in parallel. The group of first magnets 12a and the group of second magnets 12b both are preferably radially magnetized, with the magnetic poles in opposite directions. For example, the first magnets 12a have an N pole on the first coil 11a side and an S pole on the opposite side. The second magnets 12b have an S pole on the second coil 11b side and an N pole on the opposite side. More specifically, as illustrated in FIGS. 8 and 9, the directions of magnetic polarization of the respective magnets 12 are preferably set to be orthogonal to the axis C as illustrated by the respective white arrows A. The coil 11 preferably reverses its winding direction between the group of first magnets 12a and the group of second magnets 12b. For example, as illustrated in FIG. 8, if the first coil 11a is wound in the direction of the arrow B, the second coil 11b may be wound in the reverse direction. Alternatively, the first coil 11a and the second coil 11b may be wound in the same direction, and the first coil 11a and the second coil 11b may be connected so that a current flows in opposite directions. For example, as illustrated in FIG. 8, if the current flows through the first coil 11a in the direction of the arrow B, the second coil 11b may be connected so that the current flows in the direction opposite to that of the arrow B.

As described above, in the present embodiment, the movable part 3 on which the first magnets 12a are each installed to be opposed to the first coil 11a is arranged radially inside the fixed part main body 20 around which the first coil 11a is wound. The flat surface portions 11ap of the first coil 11a therefore lie within a magnetic field in directions orthogonal to radial outer surfaces 121a of the respective first magnets 12a. The second magnets 12b are similarly configured. This improves the driving efficiency and enables quick movement of the movable part 3. The flat formation of the radial outer surfaces 121a and 121b of the first magnets 12a and the second magnets 12b facilitates assembly.

If a current is passed through the coil 11 of the optical unit 1 having such a configuration, force in the axis C direction occurs on the movable part 3 due to the effect of the magnetic field from the magnets 12, and the movable part 3 moves in the direction of the axis C with respect to the fixed part 2. For example, the current flowing through the first coil 11a and the second coil 11b can be controlled to move the movable part 3 with respect to the fixed part 2. Even when the movable part 3 is moved, the radial outer surfaces of the magnets 12 are located within the hollowed portions 21a of the fixed part main body 20.

As illustrated in FIG. 3, the outer peripheries of the flange portions 31b of the movable part 3 constitute the movable-side sliding surface 31c which makes contact with the fixed-side sliding surface 24 of the fixed part main body 20. Since the fixed-side sliding surface 24 of the fixed part main body 20 is put in contact with the movable-side sliding surface 31c of the movable part 3, the movable part 3 can always move in contact with the fixed part main body 20. This can suppress a tilt of the movable part 3 with respect to the fixed part 2 and enables accurate movement of the movable part 3.

Moreover, the optical unit 1 is preferably formed symmetrically with respect to the axis C. In addition to the structure that the fixed-side sliding surface 24 of the fixed part main body 20 makes contact with the movable-side sliding surface 31*c* of the movable-side 3, the symmetrical formation of the entire optical unit 1 with respect to the axis C can locate the center of gravity on the axis C, whereby a tilt of the movable part 3 with respect to the fixed part 2 can be further suppressed.

As described above, the optical unit 1 of the present embodiment can be formed with a small size and a light weight. The driving efficiency improves, and the movable part 3 can be quickly operated. Since the fixed-side sliding surface 24 of the fixed part main body 20 and the movable-side sliding surface 31*c* of the movable part 3 are in contact even during operation, a tilt of the movable part 3 with respect to the fixed part 2 can be suppressed and the movable part 3 can be accurately moved.

Next, an optical unit according to a second embodiment will be described.

Figure 10:
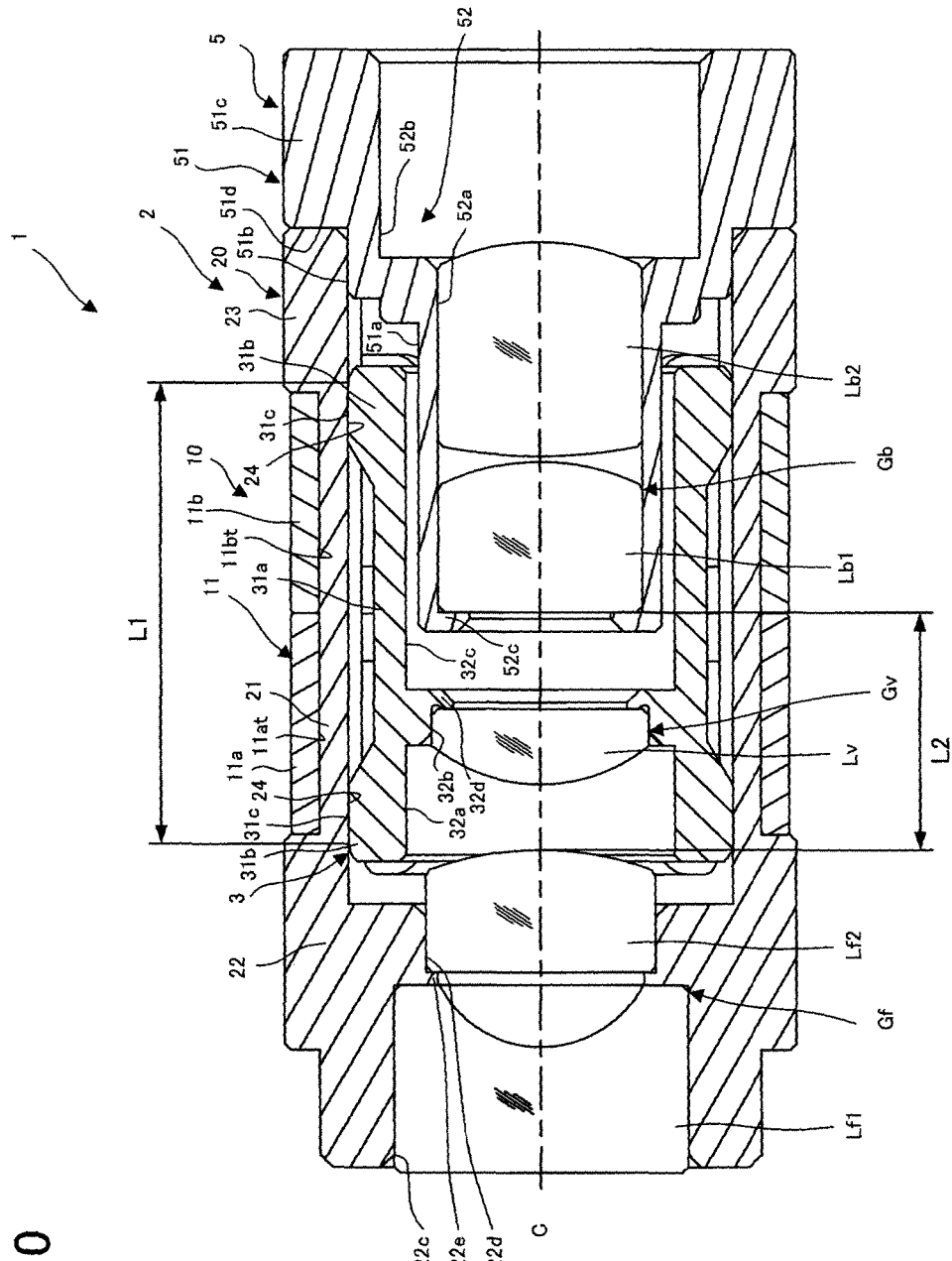
FIG. 10 is a diagram illustrating an optical unit according to a second embodiment.
Figure 11:
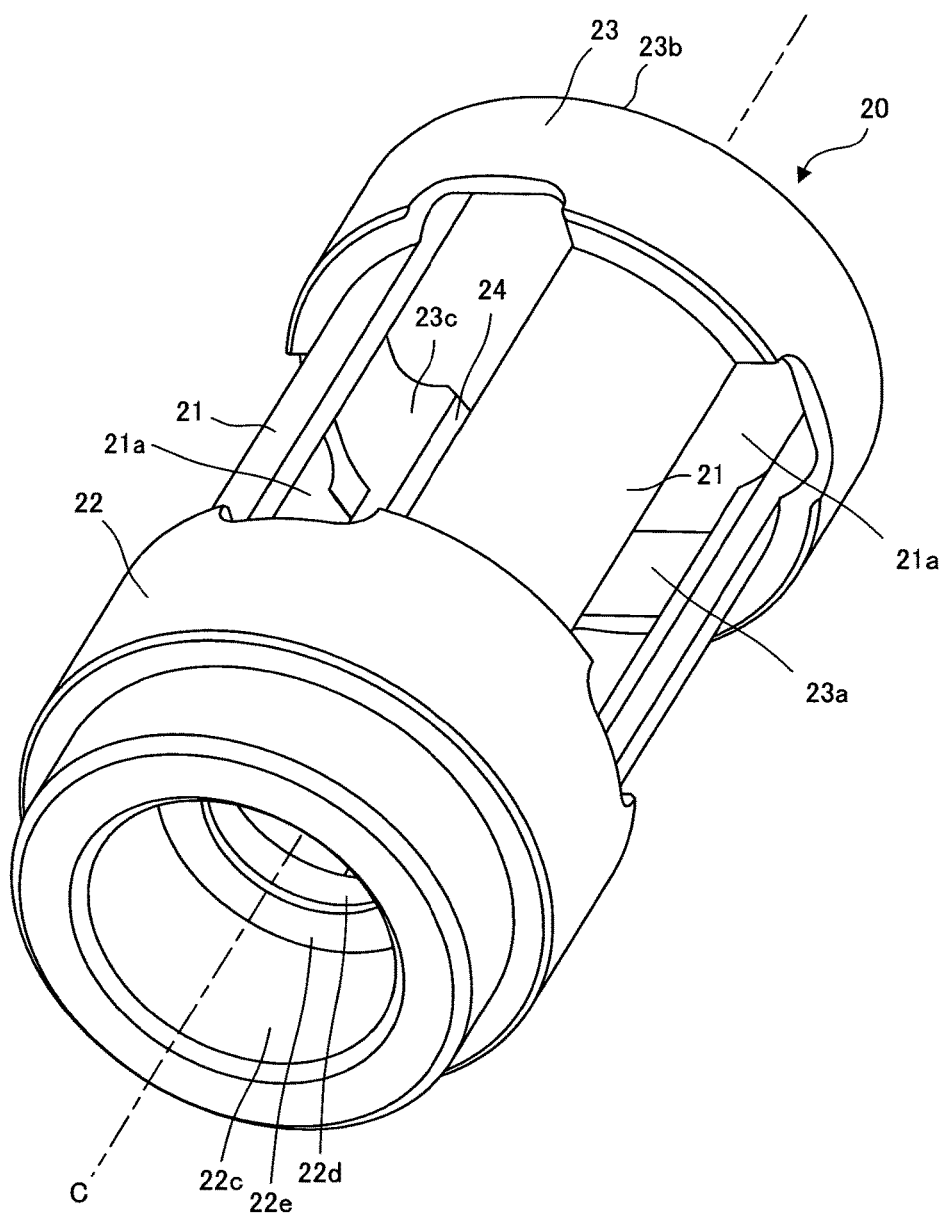
FIG. 11 is a diagram illustrating a fixed part main body of the optical unit according to the second embodiment.

FIG. 10 is a diagram illustrating the optical unit according to the second embodiment. FIG. 11 is a diagram illustrating a fixed part main body of the optical unit according to the second embodiment.

An optical unit 1 according to the second embodiment has a structure that the front frame portion 4 of the first embodiment is integrally formed with the fixed part main body 20. For example, in the second embodiment, the object-side thick portion 22 of the fixed part main body 20 is extended to the object side, and a first inner peripheral portion 22*c*, a second inner peripheral portion 22*d*, and a protrusion 22*e* are formed on the radially inner side of the object-side thick portion 22. The first inner peripheral portion 22*c* has a diameter larger than that of the second inner peripheral portion 22*d*. The protrusion 22*e* having the smallest diameter, protruding radially inward, lies between the first inner peripheral portion 22*c* and the second inner peripheral portion 22*d*.

The object-side thick portion 22 holds the object-side fixed lens group Gf. For example, in the second embodiment, the object-side thick portion 22 holds the front first lens Lf1 in the first inner peripheral portion 22*c* and the front second lens Lf2 in the second inner peripheral portion 22*d*. The image side of the front first lens Lf1 and the object side of the front second lens Lf2 are preferably held in contact with the protrusion 22*e*.

The outer peripheries of the flange portions 31*b* of the movable part 3 constitute the movable-side sliding surface 31*c* which slides over the fixed-side sliding surface 24 of the fixed part main body 20. The movable part 3 is inserted into the fixed part main body 20 with the movable-side sliding surface 31*c* in contact with the fixed-side sliding surface 24. In the second embodiment, the movable part 3 is inserted so that the first outer peripheral portion 51*a* of the rear frame portion 5 is opposed to the radially inner side of the third inner peripheral portion 32*c* of the movable part 3. In other words, at least part of the image-side fixed lens group Gb lies radially inside the third inner peripheral portion 32*c* of the movable part 3. If the movable part 3 moves closest to the object side, at least part of the object-side fixed lens group Gf lies radially inside the first inner peripheral portion 32*a* of the movable part 3.

In the optical unit 1 according to the second embodiment, as illustrated in FIG. 10, the distance L1 from the position closest to the object side to the position closest to the image side of the movable-side sliding surface 31*c* of the movable part 3 in the axis C direction is greater than the distance L2 from the emission surface of the object-side fixed lens group Gf held by the object-side thick portion 22 of the fixed part 2 to the incident surface of the image-side fixed lens group Gb held by the rear frame portion 5 of the fixed part 2. Note that the chamfered portions are not included in the distance from the position closest to the object side to the position closest to the image side of the movable-side sliding surface 31*c* of the movable part 3.

Such a configuration allows miniaturization in the axis C direction. A tilt of the movable part 3 can be suppressed to allow miniaturization in the radial direction as well. Moreover, the absence of the front frame portion 4 can reduce the parts count and the assembly processes for cost reduction.

Next, an optical unit according to a third embodiment will be described.

Figure 12:
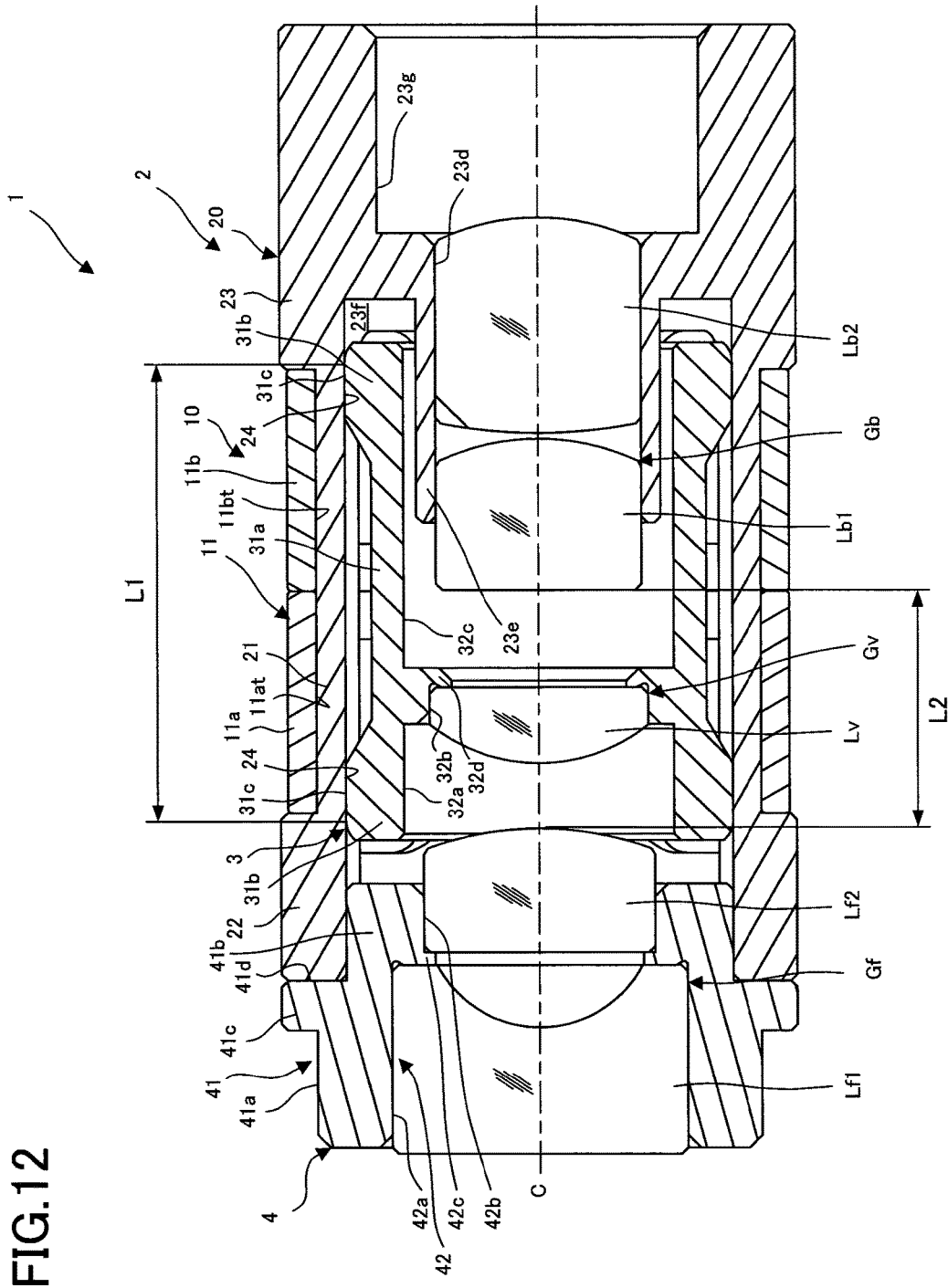
FIG. 12 is a diagram illustrating an optical unit according to a third embodiment.
Figure 13:
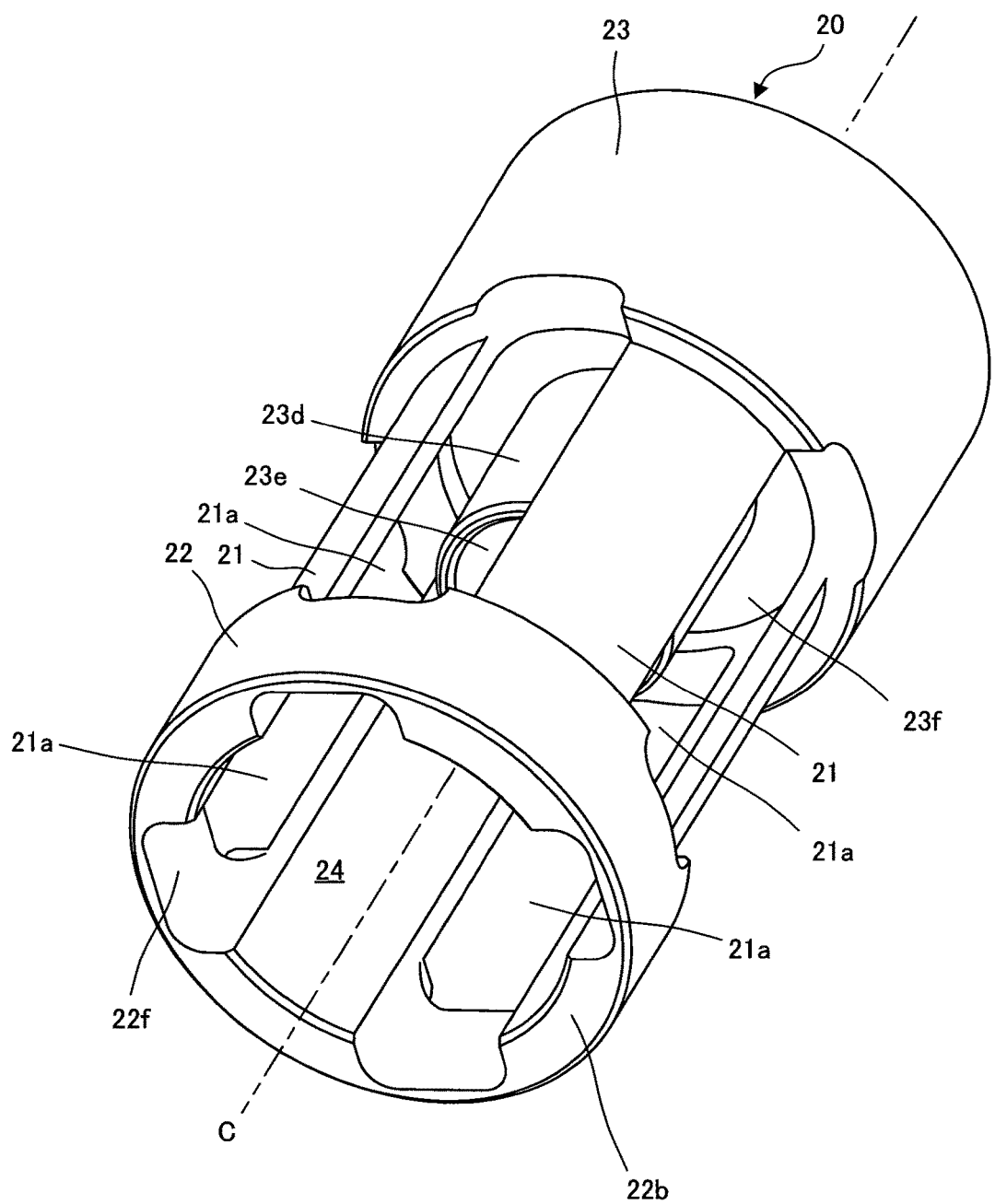
FIG. 13 is a diagram illustrating a fixed part main body of the optical unit according to the third embodiment.

FIG. 12 is a diagram illustrating the optical unit according to the third embodiment. FIG. 13 is a diagram illustrating a fixed part main body of the optical unit according to the third embodiment.

An optical unit 1 according to the third embodiment has a structure that the rear frame portion 5 of the first embodiment is integrally formed with the fixed part main body 20. For example, in the third embodiment, the image-side thick portion 23 of the fixed part main body 20 is extended to the image side, and a first inner peripheral portion 23*d*, an inner cylindrical portion 23*e*, and an axial recess 23*f* are formed on/in the radially inner side of the image-side thick portion 23.

The first inner peripheral portion 23*d* is formed to protrude radially inward from the image-side thick portion 23. The inner cylindrical portion 23*e* is a cylindrical portion extending axially from the first inner peripheral portion 23*d* to the object side. The inner cylindrical portion 23*e* of the image-side thick portion 23 holds the image-side fixed lens group Gb. For example, in the third embodiment, the image-side thick portion 23 holds the rear first lens Lb1 and the rear second lens Lb2 in the inner cylindrical portion 23*e*. The axial recess 23*f* is formed between the radial outer side of the inner cylindrical portion 23*e* and the fixed-side sliding surface 24. A part of the movable part 3 is inserted into the axial recess 23*f*. The second inner peripheral portion 23*g* having a diameter larger than that of the first inner peripheral portion 23*d* is formed on the image side of the first inner peripheral portion 23*d*. A sensor and the like may be attached to the second inner peripheral portion 23*g*. Grooves 22*f* are formed in the fixed-side sliding surface 24 on the radially inner side of the object-side thick portion 22. When the movable part 3 is assembled, the magnets 12 to be described later pass through the grooves 22*f*.

The outer peripheries of the flange portions 31*b* of the movable part 3 constitute the movable-side sliding surface 31*c* which slides over the fixed-side sliding surface 24 of the fixed part main body 20. The movable part 3 is inserted into the fixed part main body 20 with the movable-side sliding surface 31*c* in contact with the fixed-side sliding surface 24. In the third embodiment, the movable part 3 is inserted so that the inner cylindrical surface 23*e* of the fixed part main body 20 is opposed to the radially inner side of the third inner peripheral portion 32*c* of the movable part 3. In other words, at least part of the image-side fixed lens group Gb lies radially inside the third inner peripheral portion 32*c* of the movable part 3. If the movable part 3 moves closest to the object side, at least part of the object-side fixed lens group Gf lies radially inside the first inner peripheral portion 32a of the movable part 3.

In the optical unit 1 according to the third embodiment, as illustrated in FIG. 12, the distance L1 from the position closest to the object side to the position closest to the image side of the movable-side sliding surface 31c of the movable part 3 in the axis C direction is greater than the distance L2 from the emission surface of the object-side fixed lens group Gf held by the front frame portion 4 of the fixed part 2 to the incident surface of the image-side fixed lens group Gb held by the inner cylindrical portion 23e of the image-side thick portion 23 of the fixed part 2. Note that the chamfered portions are not included in the distance from the position closest to the object side to the position closest to the image side of the movable-side sliding surface 31c of the movable part 3.

Such a configuration allows miniaturization in the axis C direction. A tilt of the movable part 3 can be suppressed to allow miniaturization in the radial direction as well. Moreover, the absence of the rear frame portion 5 can reduce the parts count and the assembly processes for cost reduction.

Next, an optical unit according to a fourth embodiment will be described.

Figure 14:
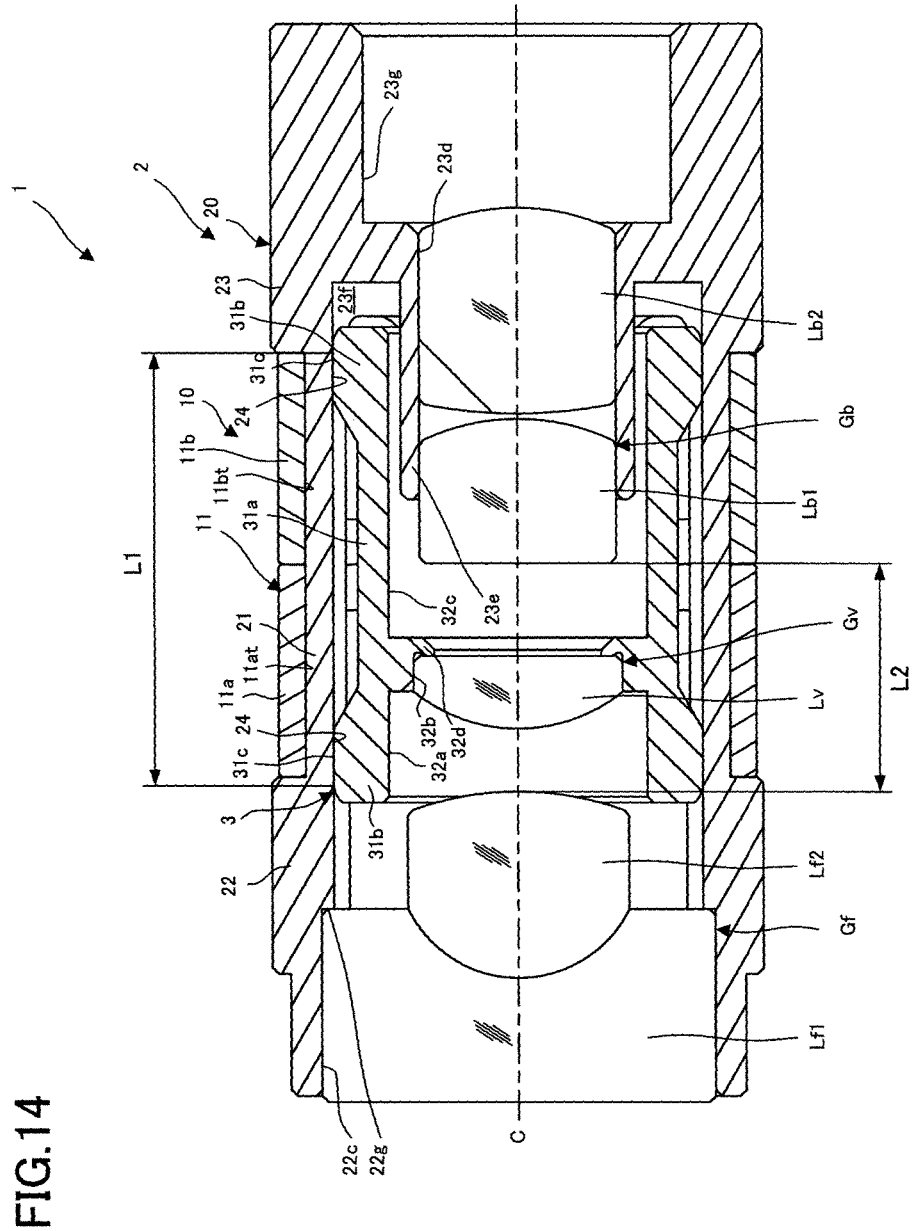
FIG. 14 is a diagram illustrating an optical unit according to a fourth embodiment.
Figure 15:
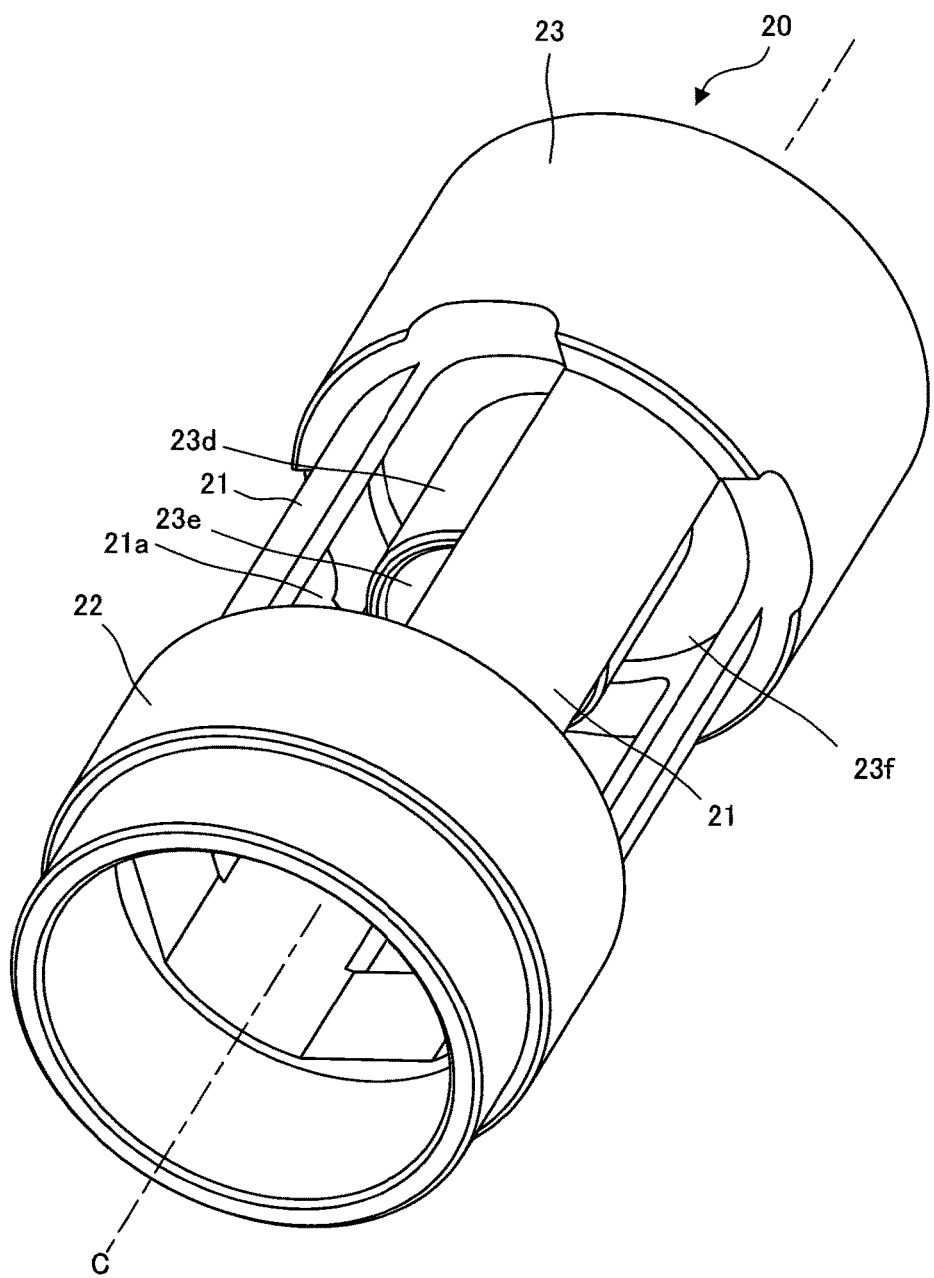
FIG. 15 is a diagram illustrating a fixed part main body of the optical unit according to the fourth embodiment.

FIG. 14 is a diagram illustrating the optical unit according to the fourth embodiment. FIG. 15 is a diagram illustrating a fixed part main body of the optical unit according to the fourth embodiment.

An optical unit 1 according to the fourth embodiment has a structure that the front frame portion 4 and the rear frame portion 5 of the first embodiment are integrally formed with the fixed part main body 20.

For example, in the fourth embodiment, the object-side thick portion 22 of the fixed part main body 20 is extended to the object side, and the first inner peripheral portion 22c and a step portion 22g are formed on the radially inner side of the object-side thick portion 22. The first inner peripheral portion 22 has a diameter larger than that of the fixed-side sliding surface 24. The step portion 22g is formed between the first inner peripheral portion 22c and the fixed-side sliding surface 24. The object-side thick portion 22 holds the object-side fixed lens group Gf. For example, in the fourth embodiment, the object-side thick portion 22 holds a cemented lens of the front first lens Lf1 and the front second lens Lf2 in the first inner peripheral portion 22c. The image side of the front first lens Lf1 is preferably held in contact with the step portion 22g.

For example, in the fourth embodiment, the image-side thick portion 23 of the fixed part main body 20 is extended to the image side, and the first inner peripheral portion 23d, the inner cylindrical portion 23e, and the axial recess 23f are formed on/in the radially inner side of the image-side thick portion 23.

The first inner peripheral portion 23d is formed to protrude radially inward from the image-side thick portion 23. The inner cylindrical portion 23e is a cylindrical portion extending axially from the first inner peripheral portion 23d to the object side. The inner cylindrical portion 23e of the image side thick portion 23 holds the image-side fixed lens group Gb. For example, in the fourth embodiment, the image-side thick portion 23 holds the rear first lens Lb1 and the rear second lens Lb2 in the inner cylindrical portion 23e. The axial recess 23f is fainted between the radially outer side of the inner cylindrical portion 23e and the fixed-side sliding surface 24. A part of the movable part 3 is inserted into the axial recess 23f. The second inner peripheral portion 23g having a diameter larger than that of the first inner peripheral portion 23d is formed on the image side of the first inner periphery side 23d. A sensor and the like may be attached to the second inner peripheral portion 23g.

The outer peripheries of the flange portions 31b of the movable part 3 constitute the movable-side sliding surface 31c which slides over the fixed-side sliding surface 24 of the fixed part main body 20. The movable part 3 is inserted into the fixed part main body 20 with the moving-side sliding surface 31c in contact with the fixed-side sliding surface 24. In the fourth embodiment, the movable part 3 is inserted so that the inner cylindrical portion 23e of the fixed part main body 20 is opposed to the radially inner side of the third inner peripheral portion 32c of the movable part 3. In other words, at least part of the image-side fixed lens group Gb lies radially inside the third inner peripheral portion 32c of the movable part 3. If the movable part 3 moves closest to the object side, at least part of the object-side fixed lens group Gf lies radially inside the first inner peripheral portion 32a of the movable part 3.

In the optical unit 1 according to the fourth embodiment, as illustrated in FIG. 14, the distance L1 from the position closest to the object side to the position closest to the image side of the movable-side sliding surface 31c of the movable part 3 in the axis C direction is greater than the distance L2 from the emission surface of the object-side fixed lens group Gb held by the first inner peripheral portion 22c of the fixed part 2 to the incident surface of the image-side fixed lens group Gb held by the inner cylindrical portion 23e of the image-side thick portion 23 of the fixed part 2. Note that the chamfered portions are not included in the distance from the position closest to the object side to the position closest to the image side of the movable-side sliding surface 31c of the movable part 3.

Such a configuration allows miniaturization in the axis C direction. A tilt of the movable part 3 can be suppressed to allow miniaturization in the radial direction as well. Moreover, the absence of the front frame portion 4 and the rear frame portion 5 can reduce the parts count and the assembly processes for cost reduction.

Next, an optical unit according to a fifth embodiment will be described.

Figure 16:
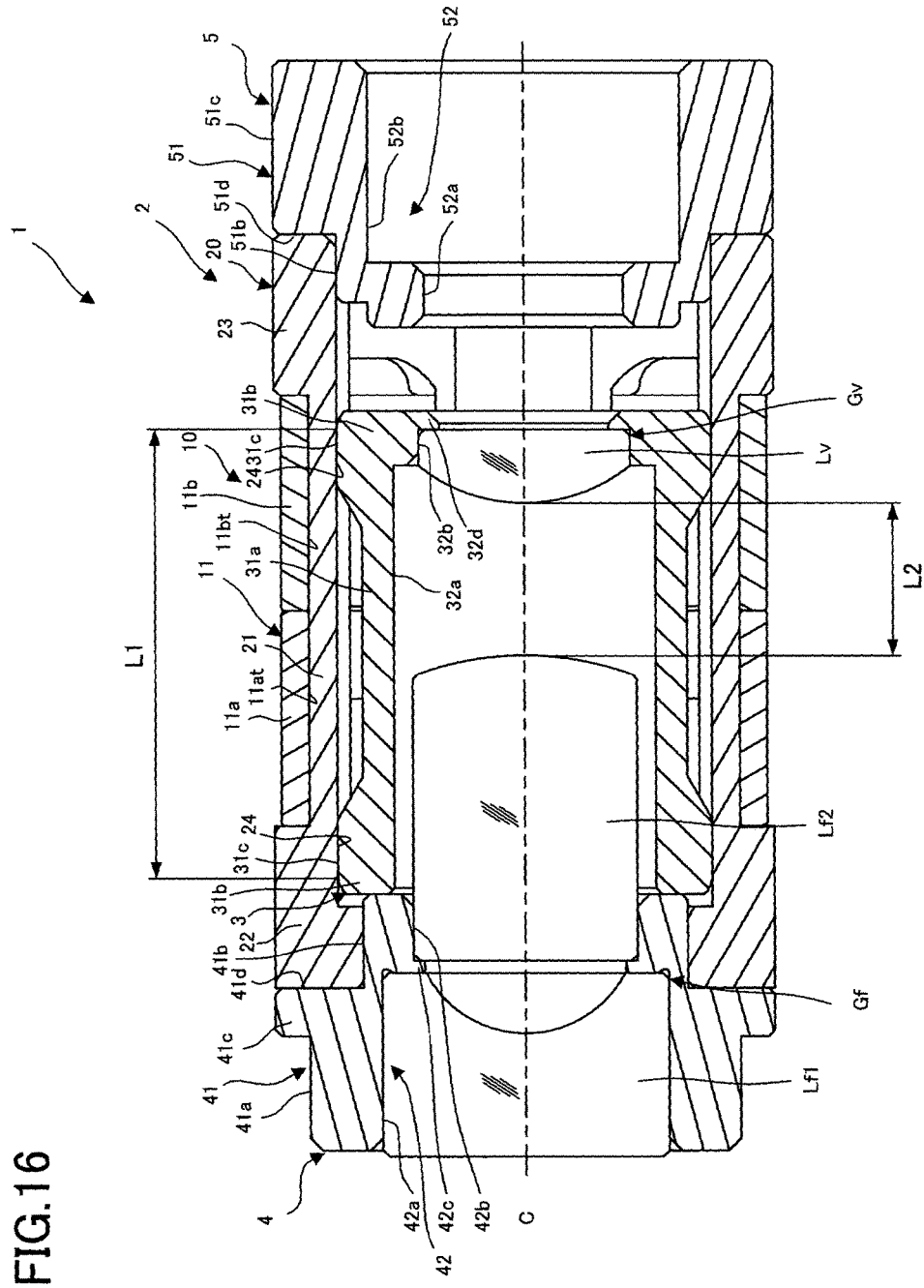
FIG. 16 is a diagram illustrating an optical unit according to a fifth embodiment.
Figure 17:
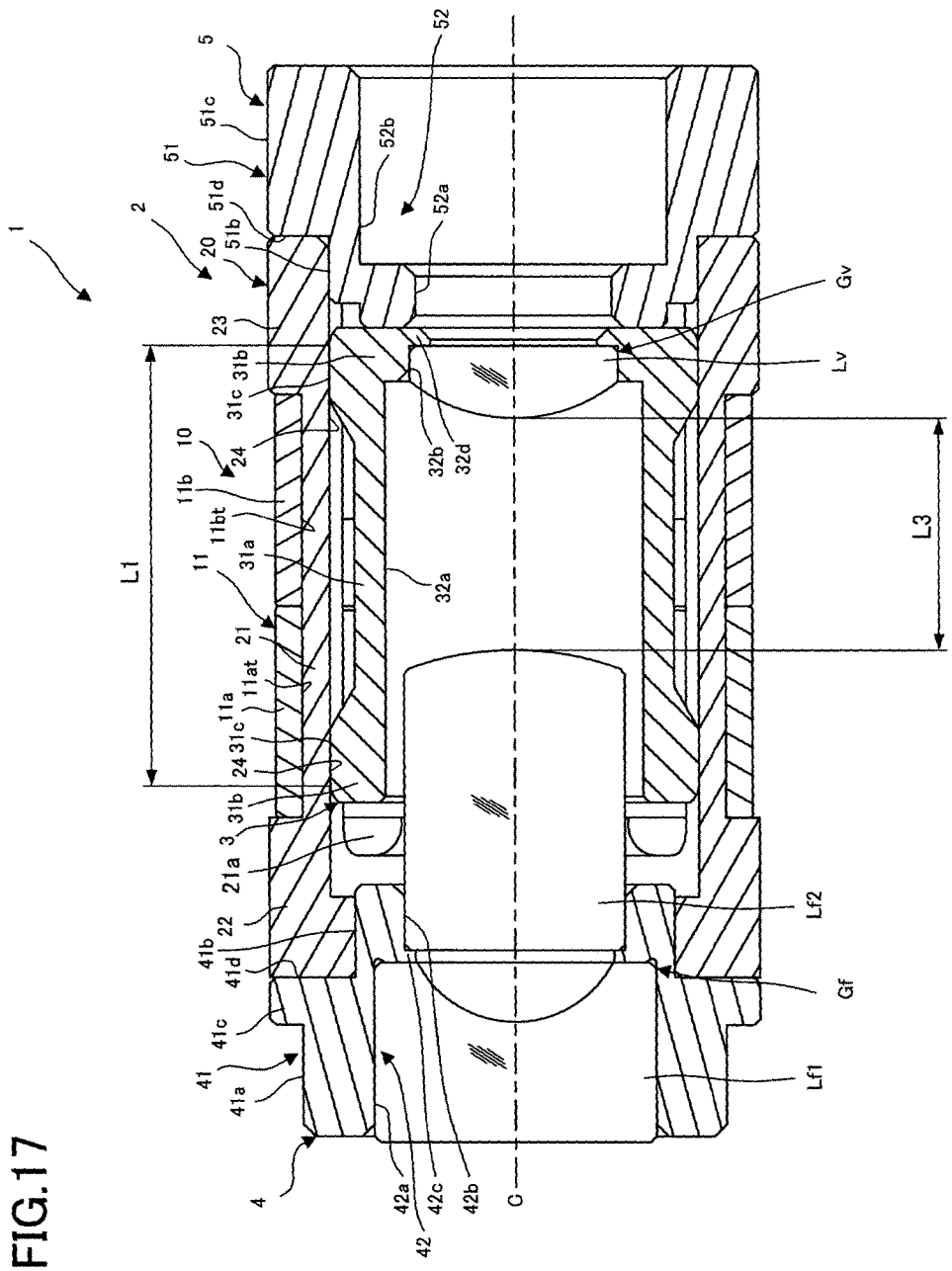
FIG. 17 is a diagram illustrating the optical unit according to the fifth embodiment after movement.
Figure 18A:
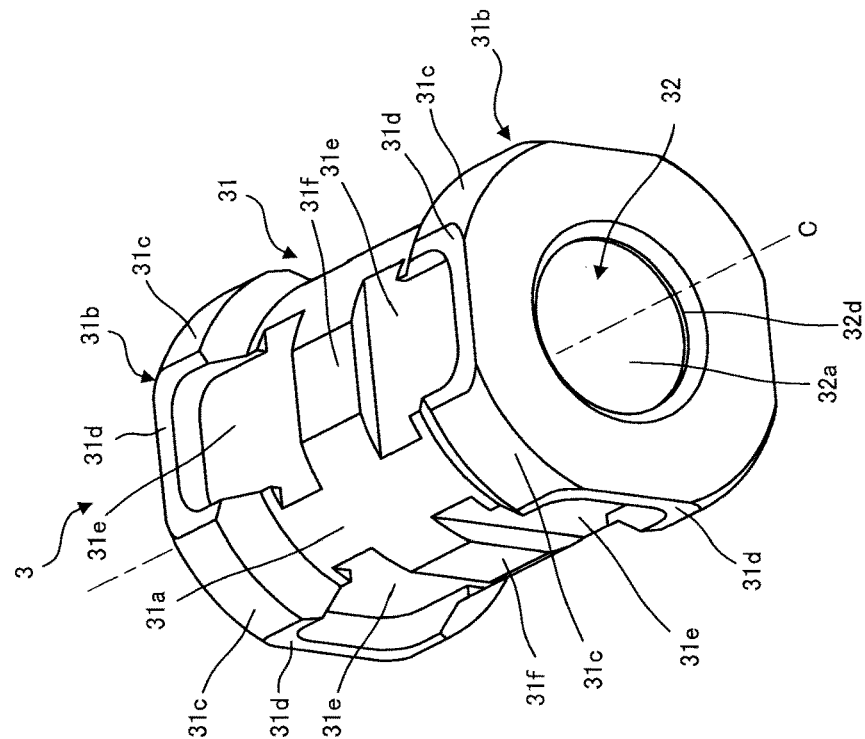
FIGS. 18A and 18B are diagrams illustrating a movable part of the optical unit according to the fifth embodiment.
Figure 18B:
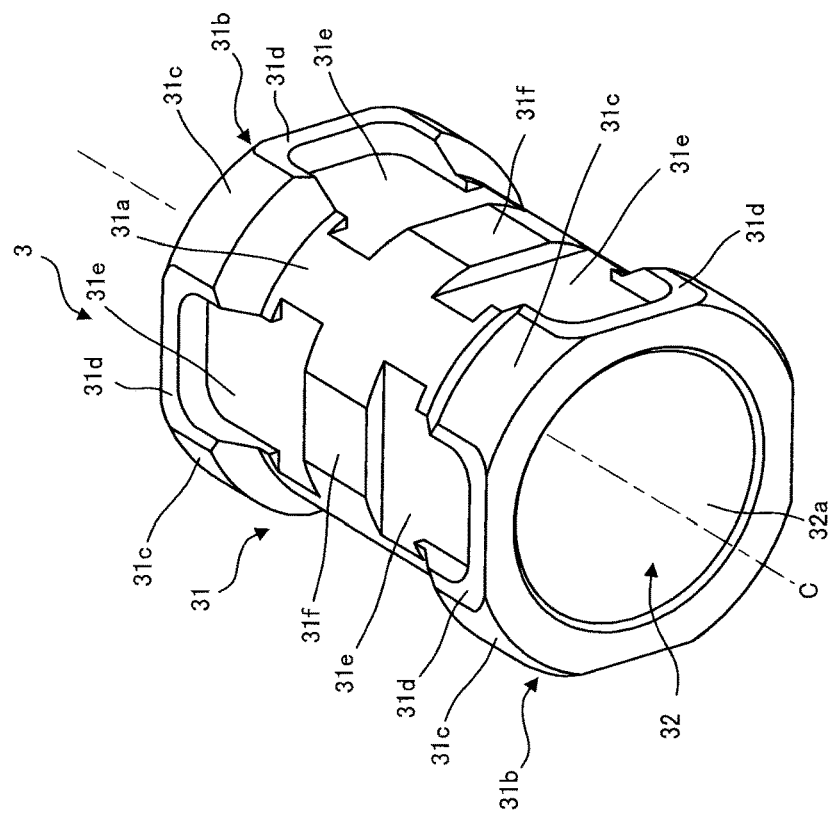
Figure 19A:
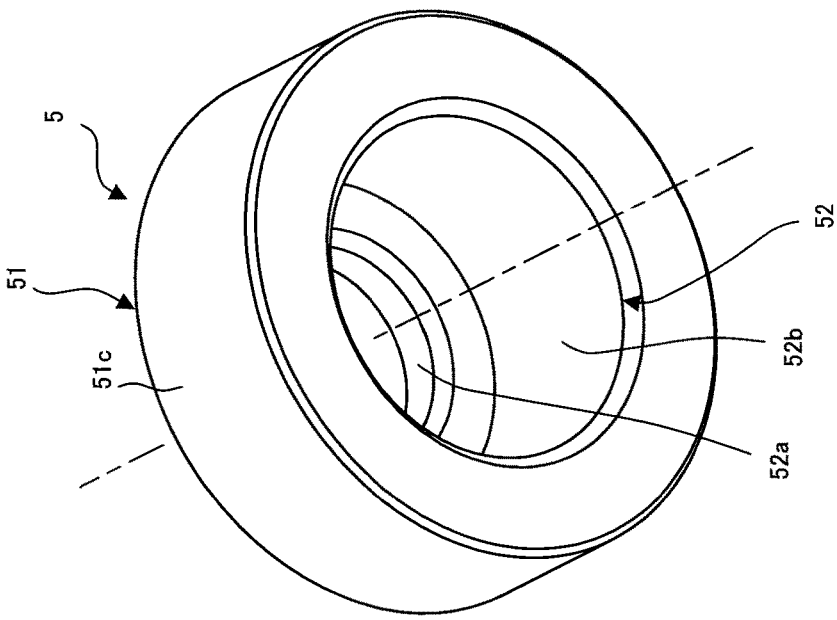
FIGS. 19A and 19B are diagrams illustrating a rear frame portion of the optical unit according to the fifth embodiment.
Figure 19B:
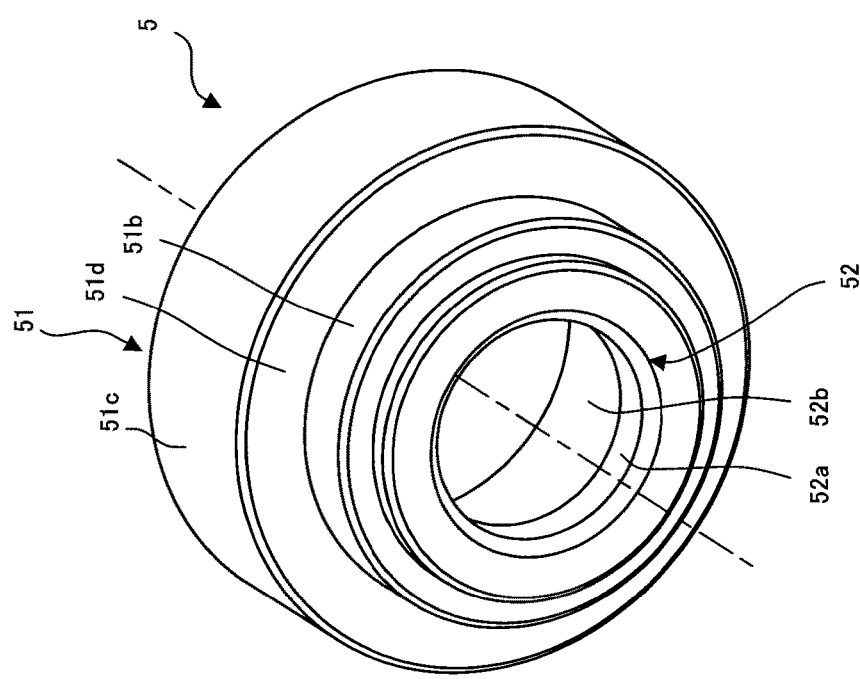

FIG. 16 is a diagram illustrating the optical unit according to the fifth embodiment, in which a movable part 3 is positioned closest to an object side. FIG. 17 is a diagram illustrating the optical unit according to the fifth embodiment after movement, in which the movable part 3 is positioned closest to an image side. FIGS. 18A and 18B are diagrams illustrating the movable part of the optical unit according to the fifth embodiment. FIGS. 19A and 19B are diagrams illustrating a rear frame portion of the optical unit according to the fifth embodiment.

As illustrated in FIG. 16, an optical unit 1 according to the fifth embodiment includes a fixed part 2, the movable part 3 which is movable with respect to the fixed part 2 and holds a moving lens group Gv, and a voice coil motor 10 which generates driving force for moving the movable part 3 with respect to the fixed part 2.

In the optical unit 1 according to the fifth embodiment, the fixed part 2 includes a fixed part main body 20, a front frame portion 4 which holds an object-side fixed lens group Gf lying on the object side of the moving lens group Gv and is attached to the object side of the fixed part main body 20, and a rear frame portion 5 which is attached to the image side of the fixed part main body 20. The optical unit 1 according to the fifth embodiment does not hold any lens group in the rear frame portion 5.

An outer peripheral portion 31 of the movable part 3 includes a cylindrical portion 31a, flange portions 31b which are to tied at both ends of the cylindrical portion 31a in an axis C direction and have an outer peripheral diameter larger than that of the cylindrical portion 31a, a movable-side sliding surface 31c which are constituted by the other peripheries of the flange portions 31b, flat surface portions 31d which are formed on part of radially outer sides of the flange portions 31b, step portions 31e which are formed between the flat surface portions 31d at both ends in the axis C direction and radially inside the cylindrical portion 31a, and cut portions 31f which are formed between the step portions 31e in the axial direction by cutting away the surface of the cylindrical portion 31a. The cylindrical portion 31a and the flange portions 31b of the movable part 3 may be configured as separate members to be assembled.

The inner peripheral portion 32 of the movable part 3 includes a first inner peripheral portion 32a, a second inner peripheral portion 32b, and a protrusion 32d. The second inner peripheral portion 32b has a diameter smaller than that of the first inner peripheral portion 32a. The protrusion 32d having the smallest diameter, protruding radially inward, lies on the image side of the second inner peripheral portion 32b.

The movable part 3 holds the moving lens group Gv. For example, in the fifth embodiment, the movable part 3 holds a moving lens Lv in the second inner peripheral portion 32b. The image side of the moving lens Lv is preferably held in contact with the protrusion 32d.

The outer peripheries of the flange portions 31b of the movable part 3 constitute the movable-side sliding surface 31c which slides over the fixed-side sliding surface 24 of the fixed part main body 20. The movable part 3 is inserted into the fixed part main body 20 with the movable-side sliding surface 31c in contact with the fixed-side sliding surface 24. In the fifth embodiment, as illustrated in FIGS. 16 and 17, the movable part 3 is inserted so that the front second lens Lf2 is opposed to the radially inner side of the first inner peripheral portion 32a of the movable part 3. In other words, at least part of the object-side fixed lens group Gf lies radially inside the first inner peripheral portion 32a of the movable part 3.

In the optical unit 1 according to the fifth embodiment, as illustrated in FIGS. 16 and 17, the distance L1 from the position closest to the object side to the position closest to the image side of the movable-side sliding surface 31c of the movable part 3 in the axis C direction is greater than the distance L3 from the emission surface of the object-side fixed lens group Gf held by the front frame portion 4 of the fixed part 2 to the incident surface of the moving lens group Gv held by the movable part 3. Note that the chamfered portions are not included in the distance from the position closest to the object side to the position closest to the image side of the movable-side sliding surface 31c of the movable part 3.

Such a configuration allows miniaturization in the axis C direction. A tilt of the movable part 3 can be suppressed to allow miniaturization in the radial direction as well.

If the movable part 3 is positioned closest to the object side illustrated in FIG. 16, one of the flange portions 31b makes contact with the front frame portion 4. If the movable part 3 is positioned closest to the image side illustrated in FIG. 17, the other flange portion 31b makes contact with the rear frame portion 5.

The range of movement can thus be set as large as possible. At the ends of the range of movement, the movable part 3 comes into contact with the front frame portion 4 or the rear frame portion 5. This allows easy positioning.

Moreover, the rear frame portion 5 illustrated in FIGS. 19A and 19B can hold a sensor and the like. This allows effective use of the space.

Next, an optical unit according to a sixth embodiment will be described.

Figure 20:
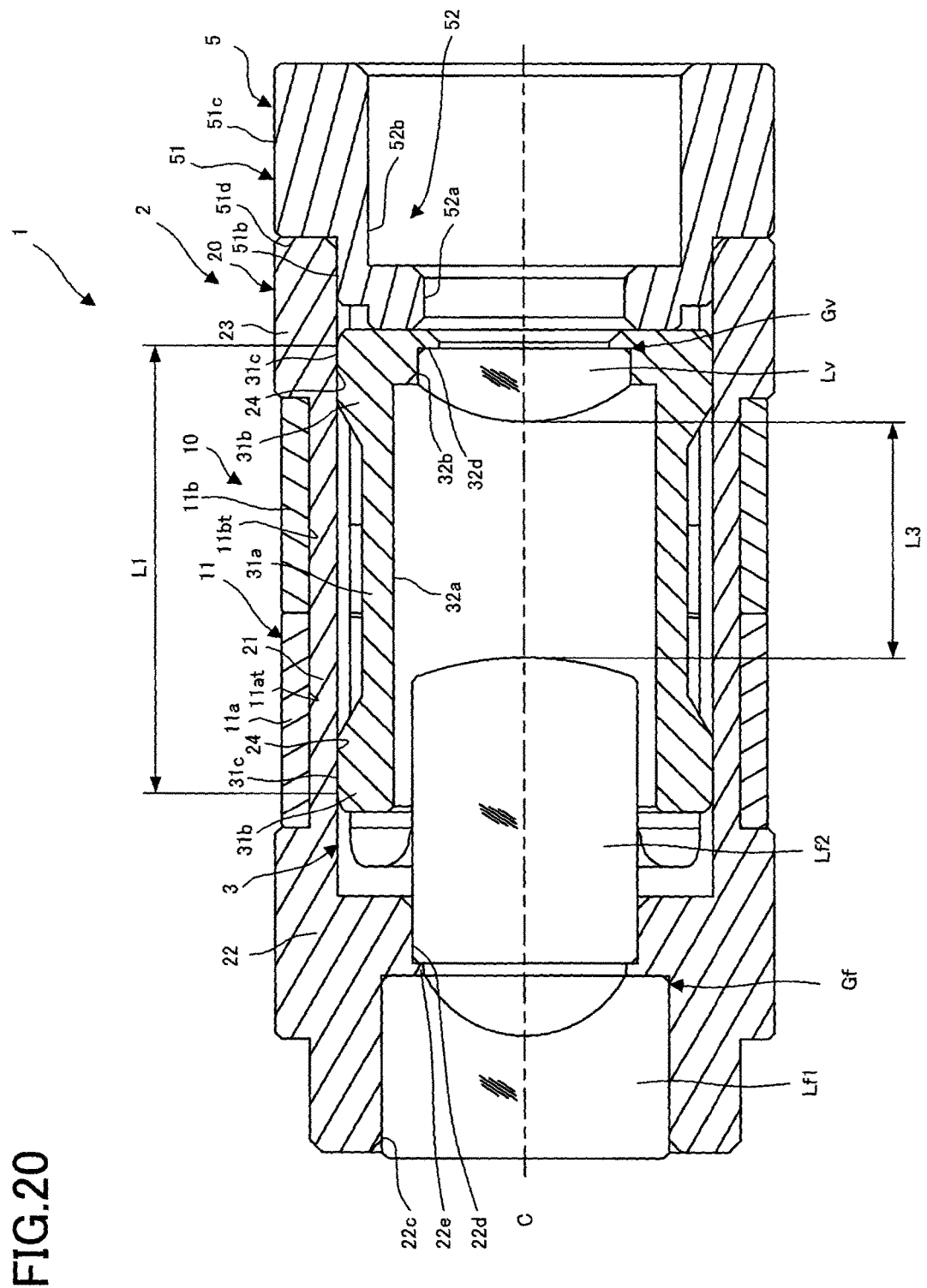
FIG. 20 is a diagram illustrating an optical unit according to a sixth embodiment.

FIG. 20 is a diagram illustrating the optical unit according to the sixth embodiment.

An optical unit 1 according to the sixth embodiment has a structure that the front frame portion 4 of the fifth embodiment is integrally formed with the fixed part main body 20. For example, in the sixth embodiment, the object-side thick portion 22 of the fixed part main body 20 is extended to the object side, and the first inner peripheral portion 22c, the second inner peripheral portion 22d, and the protrusion 22e are formed on the radially inner side of the object-side thick portion 22. The first inner peripheral portion 22c has a diameter larger than that of the second inner peripheral portion 22d. The protrusion 22e having the smallest diameter, protruding radially inward, lies between the first inner peripheral portion 22c and the second inner peripheral portion 22d. The fixed part main body 20 of the fixed part 2 of the optical unit 1 according to the sixth embodiment has the same structure as that of the fixed part main body 20 according to the second embodiment illustrated in FIG. 11. The rear frame portion 5 has the same structure as that of the rear frame portion 5 according to the fifth embodiment illustrated in FIG. 19. The movable part 3 has the same structure as that of the movable part 3 according to the fifth embodiment illustrated in FIG. 18.

The object-side thick portion 22 holds the object-side fixed lens group Gf. For example, in the sixth embodiment, the object-side thick portion 22 holds the front first lens Lf1 in the first inner peripheral portion 22c and the front second lens Lf2 in the second inner peripheral portion 22d. The image side of the front first lens Lf1 and the object side of the front second lens Lf2 are preferably held in contact with the protrusion 22e.

The outer peripheries of the flange portions 31b of the movable part 3 constitute the movable-side sliding surface 31c which slides over the fixed-side sliding surface 24 of the fixed part main body 20. The movable part 3 is inserted into the fixed part main body 20 with the movable-side sliding surface 31c in contact with the fixed-side sliding surface 24. In the sixth embodiment, as illustrated in FIG. 20, the movable part 3 is inserted so that the front second lens Lf2 is opposed to the radially inner side of the first inner peripheral portion 32a of the movable part 3. In other words, at least part of the object-side fixed lens group Gf lies radially inside the first inner peripheral portion 32a of the movable part 3.

In the optical unit 1 according to the sixth embodiment, as illustrated in FIG. 20, the distance L1 from the position closest to the object side to the position closest to the image side of the movable-side sliding surface 31c of the movable part 3 in the axis C direction is greater than the distance L3 from the emission surface of the object-side fixed lens group Gf held by the object-side thick portion 22 of the fixed part 2 to the incident surface of the moving lens group Gv held by the movable part 3. Note that the chamfered portions are not included in the distance from the position closest to the object side to the position closest to the image side of the movable-side sliding surface 31c of the movable part 3.

Such a configuration allows miniaturization in the axis C direction. A tilt of the movable part 3 can be suppressed to allow miniaturization in the radial direction as well. The absence of the front frame portion 4 can reduce the parts count and the assembly processes for cost reduction.

Next, an optical unit according to a seventh embodiment will be described.

Figure 21:
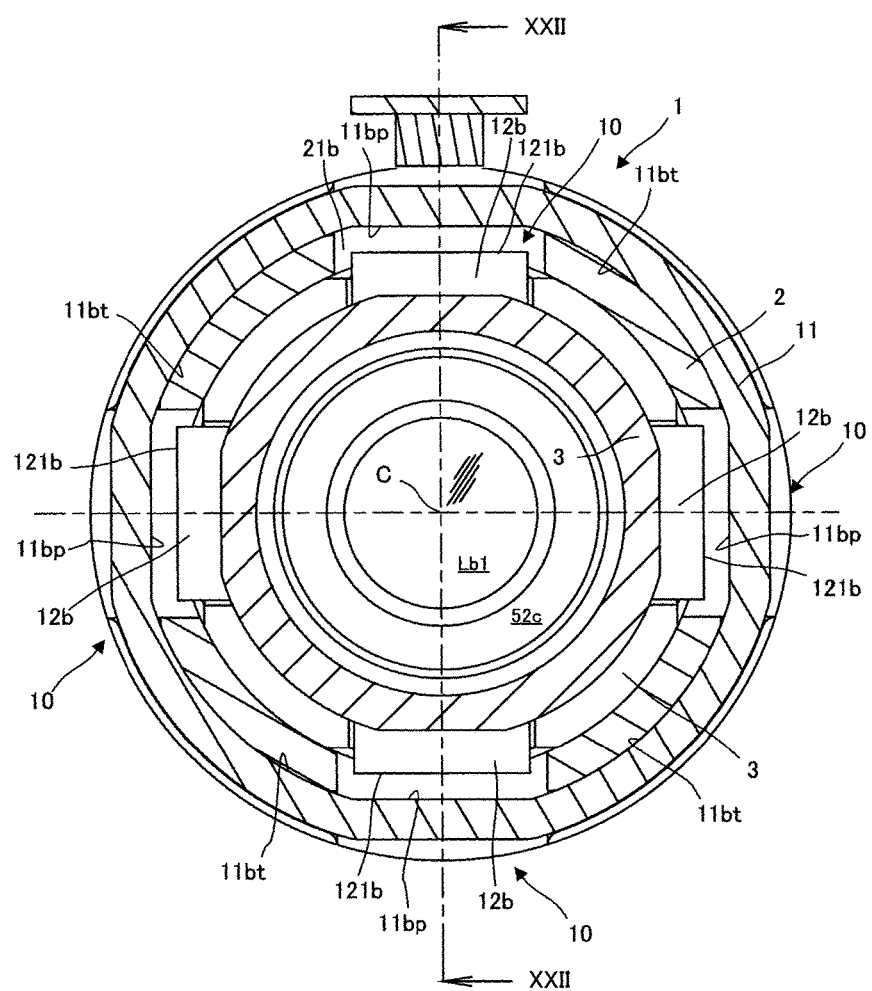
FIG. 21 is a diagram illustrating an optical unit according to a seventh embodiment.
Figure 22:
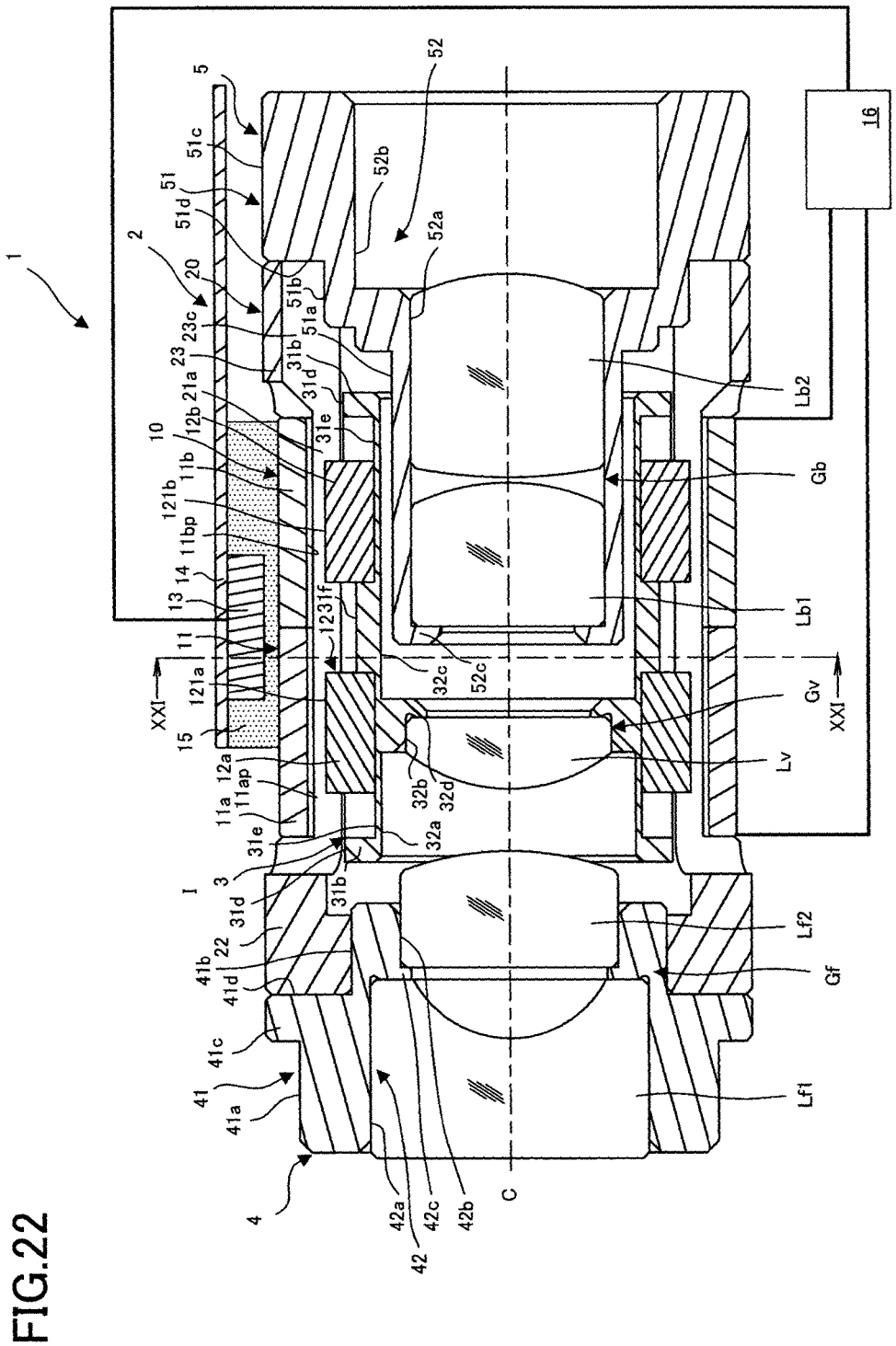
FIG. 22 is a cross-sectional view taken along the line XXII-XXII of FIG. 21.

FIG. 21 is a diagram illustrating the optical unit according to the seventh embodiment. FIG. 22 is a cross-sectional view taken along the line XXII-XXII of FIG. 21. FIG. 21 is also a cross-sectional view taken along the line XXI-XXI of FIG. 22.

As illustrated in FIG. 22, an optical unit 1 according to the seventh embodiment includes a magnetic detector 13 which detects magnetism and a drive control unit 16 which controls a current according to the magnetism detected by the magnetic detector 13, in addition to the structure of the optical unit 1 according to the fifth embodiment.

The magnetic detector 13 includes a Hall element or a magnetoresistive element (MR element), for example, and can detect magnetism. At least one magnetic detector 13 is installed to be opposed to the radially outer side of the coil 11 by a support member 14. An adhesive 15 or the like may be filled between the coil 11 and the magnetic detector 13 for support. The magnetic detector 13 is connected to the drive control unit 16 via a cable. The magnetic detector 13 may be wirelessly connected to the drive control unit 16.

The optical unit 1 includes magnets 12 which are arranged on the step portions 31e of the movable part 3. The magnetic detector 13 detects a change in the magnetic field resulting from a relative movement of the magnets 12 in the direction of the axis C. The drive control unit 16 calculates the positions of the magnets 12, i.e., the position of the movable part 3 on the basis of the change in the magnetic field detected by the magnetic detector 13. The drive control unit 16 then passes a current through the coil 11 according to a difference between a target position and the calculated magnet position.

Figure 23:
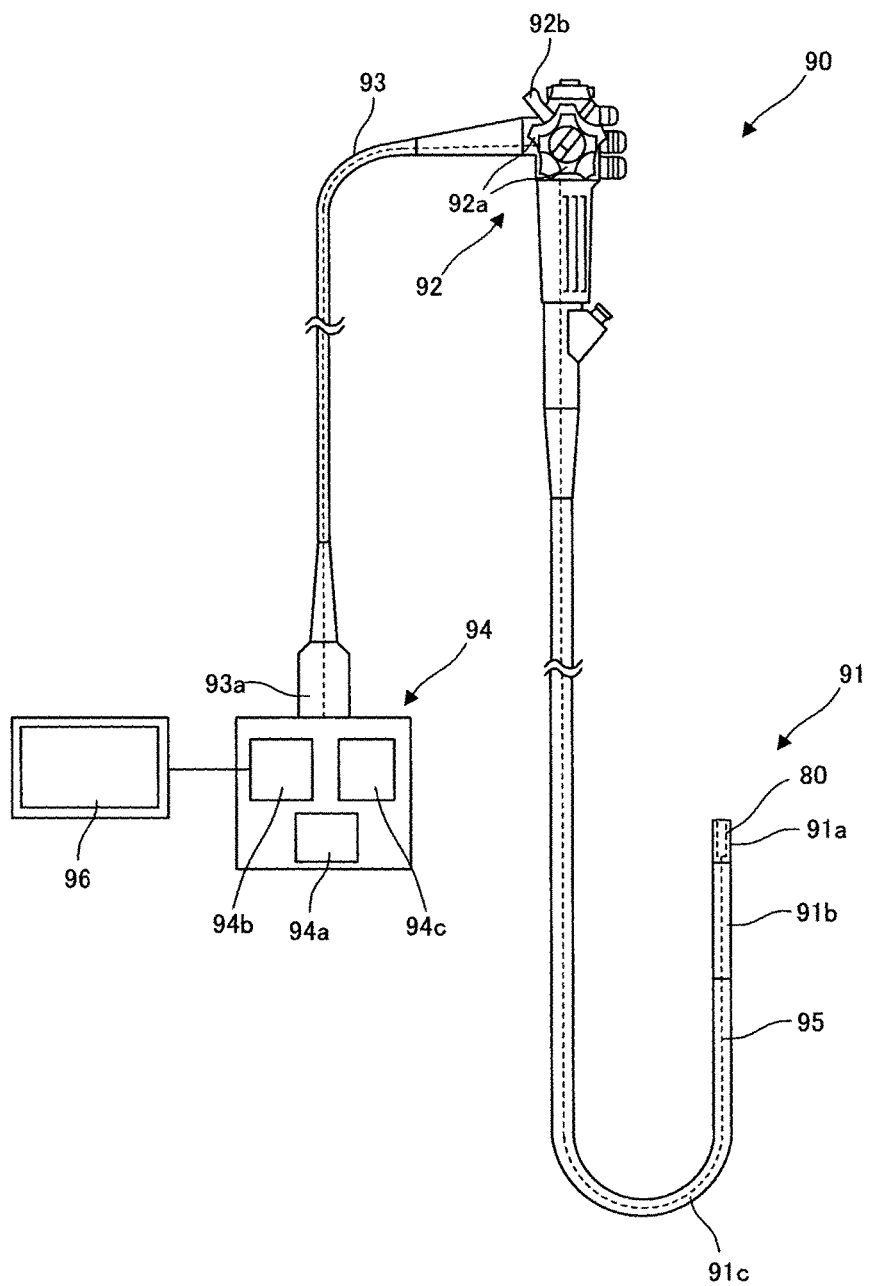
FIG. 23 is a diagram illustrating an example of an endoscope including an imaging device according to the present embodiment.

FIG. 23 is a diagram illustrating an example of an endoscope 90 including an imaging device 80 according to the present embodiment.

The endoscope 90 according to the present embodiment can be introduced into a subject such as a human body, and optically captures an image of a predetermined region to be observed in the subject. Note that the subject into which the endoscope 90 is introduced is not limited to a human body but may be other living bodies or artificial objects such as a machine and a building.

The endoscope 90 includes an insertion part 91 which is introduced into the subject, an operation part 92 which is located at the bottom of the insertion part 91, and a universal cable 93 which is a composite cable extended from the operation part 92.

The insertion part 91 includes an end section 91a which is arranged at the end, a bending section 91b which is arranged on the bottom side of the end section 91a and is bendable, and a flexible tube section 91c which is arranged on the bottom side of the bending section 91b, is connected to the end side of the operation part 92, and is flexible. The imaging device 80 is built in the end section 91a. Note that the endoscope 90 may be a rigid endoscope having no flexible tube section 91c in the insertion part 91.

The operation part 92 includes an angle operation section 92a which operates the bending state of the bending section 91b, and a zoom operation section 92b which instructs the operation of the foregoing voice coil motor 10 and performs a zoom operation of the imaging device 80. The angle operation section 92a is formed in a knob shape, and the zoom operation section 92b is formed in a lever shape. However, the angle operation section 92a and the zoom operation section 92b may take forms such as a volume switch and a push switch, respectively.

The universal cord 93 is a member for connecting the operation part 92 with an external apparatus 94. The universal cord 93 is connected to the external apparatus 94 via a connector 93a. The external apparatus 94 includes a drive control unit 94a which controls the bending state of the bending section 91b, an image control unit 94b which controls the imaging device 80, an unillustrated light source unit, and a light source control unit 94c which controls the light source unit.

Cables 95 such as a wire, an electrical line, and an optical fiber are inserted through the insertion part 91, the operation part 92, and the universal cord 93. The wire connects the drive control unit 94a arranged in the external apparatus 94 with the operation part 92 and the bending section 91b. The electrical line electrically connects the imaging device 80 with the operation part 92 and the image control unit 94b. The optical fiber optically connects the light source with the operation part 92 and the light source control unit 94c.

The drive control unit 94a includes an actuator and controls the bending state of the bending section 91b by extending and retracting the wire. The image control unit 94b performs a drive control on the voice coil motor 10 built in the imaging device 80 and processes an image captured by an imaging device. The image processed by the image control unit 94b is displayed on an image display unit 96. The light source control unit 94c controls the brightness and the like of the light source projected from the end section 91a.

Note that the operation part 92 and the external apparatus 94 may be formed as members separate from the insertion part 91, and may operate and control the insertion part 91 by remote control.

Since the imaging device 80 according to the present embodiment is employed, the endoscope 90 having such a configuration is small in size, can perform quick zooming, and is suitable to capture a moving image.

As described above, the optical unit 1 according to the present embodiment includes the fixed part 2 which holds at least either the object-side fixed lens group Gf or the image-side fixed lens group Gb and has a cylindrical shape about the predetermined axis C at least in part, the movable part 3 which holds the moving lens group Gv between the object-side fixed lens group Gf and the image-side fixed lens group Gb, is arranged radially inside the fixed part 2, and has a cylindrical shape about the axis C, and the voice coil motor 10 which can relatively move the movable part 3 with respect to the fixed part 2 in the axis C direction by using the coil 11 which is arranged on the fixed part 2 and the magnets 12 which are arranged on the movable part 3 and magnetically polarized in directions orthogonal to the axis C. The movable part 3 includes the movable-side sliding surface 31c which can slide over the inner periphery of the fixed part 2. The distance L1 from the position closest to the object side to the position closest to the image side of the movable-side sliding surface 31c in the axis C direction of the movable part 3 is greater than the distance from the emission surface of the object-side fixed lens group Gf held by the fixed part 2 to the incident surface of the image-side fixed lens group Gb held by the fixed part 2. A small-sized light-weighted optical unit 1 in which the movable part 3 is driven to move back and forth with respect to the fixed part 2 by using the voice coil motor 10 can thus be provided.

According to the optical unit 1 of the present embodiment, the fixed part 2 includes the fixed part main body 20 which holds the image-side fixed lens group Gb and includes the fixed-side sliding surface 24 and on which the coil 11 is arranged, and the front frame portion 4 which holds the object-side fixed lens group Gf and is attached to the object side of the fixed part main body 20 with the axis C at the center. The parts count and the assembly processes can thus be reduced for cost reduction.

According to the optical unit 1 of the present embodiment, the fixed part 2 includes the fixed part main body 20 which holds the object-side fixed lens group Gf and includes the fixed-side sliding surface 24 and on which the coil 11 is arranged, and the rear frame portion 5 which holds the image-side fixed lens group Gb and is attached to the image side of the fixed part main body 20 with the axis C at the center. The parts count and the assembly processes can thus be reduced for cost reduction.

According to the optical unit 1 of the present embodiment, the fixed part 2 includes the fixed part main body 20 which includes the fixed-side sliding surface 24 and on which the coil 11 is arranged, the front frame portion 4 which holds the object-side fixed lens group Gf and is attached to the object side of the fixed part main body 20 with the axis Cat the center, and the rear frame portion 5 which holds the image-side fixed lens group Gb and is attached to the image side of the fixed part main body 20 with the axis C at the center. The degrees of freedom of design can thus be increased.

According to the optical unit 1 of the present embodiment, the fixed part 2 includes the fixed part main body 20 which holds the object-side fixed lens group Gf and the image-side fixed lens group Gb and includes the fixed-side sliding surface 24 and on which the coil 11 is arranged. The parts count and the processing processes can thus be reduced for cost reduction.

The optical unit 1 according to the present embodiment includes the fixed part 2 which holds the object-side fixed lens group Gf and has a cylindrical shape about a predetermined axis C at least in part, the movable part 3 which holds the moving lens group Gv lying on the image side of the object-side fixed lens group Gf, is arranged radially inside the fixed part 2, and has a cylindrical shape about the axis C, and the voice coil motor 10 which can relatively move the movable part 3 with respect to the fixed part 2 by using the coil 11 which is arranged on the fixed part 2 and the magnets 12 which are arranged on the movable part 3 and magnetically polarized in directions orthogonal to the axis C. The movable part 3 includes the movable-side sliding surface 31c which can slide over the inner periphery of the fixed part 2. The distance L1 from the position closest to the object side to the position closest to the image side of the movable-side sliding surface 31c in the axis C direction is greater than the distance L3 from the emission surface of the object-side fixed lens group Gf held by the fixed part 2 to the incident surface of the moving lens group Gb held by the movable part 3. A small-sized light-weighted optical unit 1 in which the movable part 3 is driven to move back and forth with respect to the fixed part 2 by using the voice coil motor 10 can thus be provided.

According to the optical unit 1 of the present embodiment, the fixed part 2 includes the fixed part main body 20 which includes the fixed-side sliding surface 24 and on which the coil 11 is arranged, and the front frame portion 4 which holds the object-side fixed lens group Gf and is attached to the object side of the fixed part main body 20 with the axis C at the center. The parts count and the assembly processes can thus be reduced for cost reduction.

According to the optical unit 1 of the present embodiment, the fixed part 2 includes the fixed part main body 20 which holds the object-side fixed lens group Gf and includes the fixed-side sliding surface 24 and on which the coil 11 is arranged. The parts count and the assembly processes can thus be reduced for further cost reduction.

According to the optical unit 1 of the present embodiment, the coil 11 is wound about the axis C. The sliding axis of the movable part and the axis of action of the thrust force generated by the voice coil motor can thus be matched for stable driving.

According to the optical unit 1 of the present embodiment, the fixed-side sliding surface 24 of the fixed part 2 is formed to be circumferentially divided. The optical unit 1 can thus be reduced in size by a simple structure.

According to the optical unit 1 of the present embodiment, a plurality of magnets 12 is arranged symmetrically with respect to the axis C. The driving force can thus be stably increased.

According to the optical unit 1 of the present embodiment, the magnets 12 include the group of first magnets 12a and the group of second magnets 12b which adjoin in the axial direction. The group of first magnets 12a have the same magnetic polarization direction. The group of second magnets 12b have the same magnetic polarization direction. The magnetic polarization direction of the first magnets 12a and the magnetic polarization direction of the adjoining second magnets 12b are opposite to each other. The coil 11 includes the first coil 11a opposed to the group of first magnets 12a and the second coil 11b opposed to the group of second magnets 12b. The first coil 11a and the second coil 11b are connected so that a current flows in opposite directions. The driving force can thus be increased.

According to the optical unit 1 of the present embodiment, the first coil 11a and the second coil 11b are in contact in the axis C direction. This allows further miniaturization.

According to the optical unit 1 of the present embodiment, the first magnets 12a and the second magnets 12b are separated in the axis C direction. Stable driving force can thus be formed regardless of the position of the movable part 3.

The optical unit 1 according to the present embodiment includes the magnetic detection unit 13 which detects the magnetism of the first magnets 12a and the second magnets 12b radially outside the outer periphery of the first coil 11a and the second coil 11b, and the control unit 16 which controls the driving current flowing through the coil 11 according to a detection value detected by the magnetic detection unit 13. The driving speed and a stop position of the movable part 3 can thus be accurately controlled.

According to the optical unit 1 of the present embodiment, the magnetic detection unit 13 is supported by the fixed part 2 and detects a change in magnetism resulting from the relative movement of the movable part 3 with respect to the fixed parts 2 in the axis C direction. The driving speed and the stop position of the movable part 3 can thus be detected more accurately.

The endoscope 90 according to the present embodiment includes the foregoing optical unit 1 and the imaging device 80 on which light passed through the optical unit 1 is incident. A small-sized endoscope which is capable of quick zooming and suitable to capture a moving image can thus be provided.

The present invention is not limited to this embodiment. That is, while the description of the embodiment includes many specific details for illustrative purposes, it will be understood by those skilled in the art that different variations and modifications may be made to such details without departing from the scope of the present invention. The exemplary embodiment of the present invention has been described without losing the generality of or limiting the claimed inventions.

REFERENCE SIGNS LIST

1: Optical unit
2: Fixed part
3: Movable part
4: Front frame portion (fixed part)
5: Rear frame portion (fixed part)
10: Voice coil motor
11: Coil
12: Magnet
80: Imaging device
90: Endoscope
91: Insertion part
Gf: Object-side fixed lens group
Gb: Image-side fixed lens group
Gv: Moving lens group

The invention claimed is:

1. An optical unit comprising:
a fixed part that holds at least either an object-side fixed lens group or an image-side fixed lens group and has a cylindrical shape about a predetermined axis at least in part;
a movable part that holds a moving lens group between the object-side fixed lens group and the image-side fixed lens group, is arranged radially inside the fixed part, and has a cylindrical shape about the axis; and
a voice coil motor that is capable of relatively moving the movable part with respect to the fixed part in the axial direction by using a coil arranged on the fixed part and a magnet arranged on the movable part, the magnet being magnetically polarized in a direction orthogonal to the axis, wherein
the movable part includes a movable-side sliding surface that is capable of sliding over an inner periphery of the fixed part, and
a distance from a position closest to an object side to a position closest to an image side of the movable-side sliding surface in the axial direction of the movable part is greater than a distance from an emission surface of the object-side fixed lens group held by the fixed part to an incident surface of the image-side fixed lens group held by the fixed part.

2. The optical unit according to claim 1, wherein the fixed part includes
a fixed part main body that holds the image-side fixed lens group and includes a fixed-side sliding surface and on which the coil is arranged, and
a front frame portion that holds the object-side fixed lens group and is attached to an object side of the fixed part main body with the axis at a center.

3. The optical unit according to claim 1, wherein the fixed part includes
a fixed part main body that holds the object-side fixed lens group and includes a fixed-side sliding surface and on which the coil is arranged, and
a rear frame portion that holds the image-side fixed lens group and is attached to an image side of the fixed part main body with the axis at a center.

4. The optical unit according to claim 1, wherein the fixed part includes
a fixed part main body that includes a fixed-side sliding surface and on which the coil is arranged, a front frame portion that holds the object-side fixed lens group and is attached to an object side of the fixed part main body with the axis at a center, and
a rear frame portion that holds the image-side fixed lens group and is attached to an image side of the fixed part main body with the axis at the center.

5. The optical unit according to claim 1, wherein the fixed part includes a fixed part main body that holds the object-side fixed lens group and the image-side fixed lens group and includes a fixed-side sliding surface and on which the coil is arranged.

6. The optical unit according to claim 1, wherein the coil is wound about the axis.

7. The optical unit according to claim 1, wherein the fixed-side sliding surface of the fixed part is formed to be circumferentially divided.

8. The optical unit according to claim 1, wherein a plurality of magnets is symmetrically arranged about the axis.

9. The optical unit according to claim 1, wherein:
the magnet (s) includes/include a group of first magnets and a group of second magnets adjoining in the axial direction;
the group of first magnets have the same magnetic polarization direction;
the group of second magnets have the same magnetic polarization direction;
the magnetic polarization direction of the first magnets and the magnetic polarization direction of the adjoining second magnets are opposite to each other;
the coil includes a first coil opposed to the group of first magnets and a second coil opposed to the group of second magnets; and
the first coil and the second coil are connected so that a current flows in opposite directions.

10. The optical unit according to claim 9, wherein the first coil and the second coil are in contact in the axial direction.

11. The optical unit according to claim 9, wherein the first magnets and the second magnets are separated in the axial direction.

12. The optical unit according to claim 9, comprising:
a magnetic detection unit that detects magnetism of the first magnets and the second magnets radially outside an outer periphery of the first coil and the second coil; and
a control unit that controls a driving current flowing through the coil according to a detection value detected by the magnetic detection unit.

13. The optical unit according to claim 12, wherein the magnetic detection unit is supported by the fixed part and detects a change in magnetism resulting from a relative movement of the movable part with respect to the fixed part in the axial direction.

14. An endoscope comprising:
the optical unit according to claim 1; and
an imaging device on which light passed through the optical unit is incident.

15. An optical unit comprising:
a fixed part that holds an object-side fixed lens group and has a cylindrical shape about a predetermined axis at least in part;
a movable part that holds a moving lens group lying on an image side of the object-side fixed lens group, is arranged radially inside the fixed part, and has a cylindrical shape about the axis; and
a voice coil motor that is capable of relatively moving the movable part with respect to the fixed part in the axial direction by using a coil arranged on the fixed part and a magnet arranged on the movable part, the magnet being magnetically polarized in a direction orthogonal to the axis, wherein the movable part includes a movable-side sliding surface that is capable of sliding over an inner periphery of the fixed part, and a distance from a position closest to an object side to a position closest to an image side of the movable-side sliding surface in the axial direction of the movable part is greater than a distance from an emission surface of the object-side fixed lens group held by the fixed part to an incident surface of the moving lens group held by the movable part.

16. The optical unit according to claim 15, wherein the fixed part includes a fixed part main body that includes a fixed-side sliding surface and on which the coil is arranged, and a front frame portion that holds the object-side fixed lens group and is attached to an object side of the fixed part main body with the axis at a center.

17. The optical unit according to claim 15, wherein the fixed part includes a fixed part main body that holds the object-side fixed lens group and includes the fixed-side sliding surface and on which the coil is arranged.

18. The optical unit according to claim 15, wherein the coil is wound about the axis.

* * * * *